US012723094B2

(12) United States Patent
Hackel et al.

(10) Patent No.: US 12,723,094 B2
(45) Date of Patent: Sep. 1, 2026

(54) ANTI-DR5 POLYPEPTIDES AND METHODS OF USE THEREOF

(71) Applicant: Regents of the University of Minnesota, Minneapolis, MN (US)

(72) Inventors: Benjamin Hackel, Minneapolis, MN (US); Jonathan N. Sachs, Minneapolis, MN (US); Nagamani Vunnam, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 999 days.

(21) Appl. No.: 17/908,175

(22) PCT Filed: Mar. 3, 2021

(86) PCT No.: PCT/US2021/020719
§ 371 (c)(1),
(2) Date: Aug. 30, 2022

(87) PCT Pub. No.: WO2021/178569
PCT Pub. Date: Sep. 10, 2021

(65) Prior Publication Data

US 2023/0312737 A1 Oct. 5, 2023

Related U.S. Application Data

(60) Provisional application No. 62/985,105, filed on Mar. 4, 2020.

(51) Int. Cl.
*C07K 16/28* (2006.01)
*A61K 38/00* (2006.01)

(52) U.S. Cl.
CPC .......... *C07K 16/2878* (2013.01); *A61K 38/00* (2013.01); *C07K 2317/76* (2013.01); *C07K 2318/20* (2013.01)

(58) Field of Classification Search
None
See application file for complete search history.

(56) References Cited

U.S. PATENT DOCUMENTS

2013/0095033 A1 4/2013 Chang et al.
2017/0319613 A1 11/2017 Shiboleth et al.
2018/0016344 A1 1/2018 Moore et al.

OTHER PUBLICATIONS

Senkow et al. "Evaluation of High Affinity Scaffolds from High-Throughput Discover and Targeting DR5 and TNFR1" Biophysical Journal 112:530A. (Year: 2017).*
Woldring et al. "A gradient of sitewise diversity promotes evolutionary fitness for binder discovery in a three-helix bundle protein scaffold" Biochemistry 56:1656-1671. (Year: 2017).*
Dubuisson, A. , et al., "Antibodies and Derivatives Targeting DR4 and DR5 for Cancer Therapy", Antibodies (Basel) 6(16), doi:10.3390/antib6040016, 1-31 (2017).
Gunneriusson, E , et al., "Affinity maturation of a Taq DNA polymerase specific affibody by helix shuffling", Protein Engineering 12 (10), 873-878 (1999).
Jeong, W. , et al., "Connecting two proteins using a fusion alpha helix stabilized by a chemical cross linker", Nat. Commun. 7 (11031), doi: 10.1038/ncomms11031, 1-9 (2016).
Patent Cooperation Treaty , International Search Report and Written Opinion for PCT/US2021/020719, 17 pages, dated Sep. 14, 2021.
Senkow, T , et al., "Evaluation of High Affinity Scaffolds from High-Throughput Discovery and Targeting DR5 and TNFR1", Biophysical J 112(3), Supp 1, p. 530a (2017).
Tendulkar, A. , et al., "Characterization and sequence prediction of structural variations in alpha-helix", BMC Bioinformatics 12 (Suppl 1): S20, 1-8 (2011).
UNITPROTKB—A0A2V5SIX3, "Cysteine—tRNA ligase" https://www.uniprot.org/uniprot/A0A2V5SIX3, 4 pages, Last Modified on Sep. 12, 2018 (online); Retrieved on May 21, 2021.
Vunnam, N , et al., "Discovery of Tumor Necrosis Factor Receptor Binders using Yeast Surface Display", Abstract, The FASEB Journal / vol. 32, Issue S1 / p. 798.18-798.18, https://faseb.onlinelibrary.wiley.com/doi/10.1096/fasebj.2018.32.1_supplement.798.18 1 page (2018).
Vunnam, N , et al., "Discovery of Tumor Necrosis Factor Receptors Binders using Yeast surface display", ASBMB Annual Meeting, San Diego, CA, Poster, 5 pages (2018).
Vunnam, N , et al., "Noncompetitive Allosteric Antagonism of Death Receptor 5 by a Synthetic Affibody Ligand", Biochemistry 59 (40), 3856-3868 (2020).
Vunnam, N , et al., "Noncompetitive allosteric antagonism of death receptor 5 by an affi bodydiscovered via yeast display", Abstract, The FASEB Journal vol. 34, Issue S1, p. 1-1, https://faseb.onlinelibrary.wiley.com/doi/10.1096/fasebj.2020.34.s1.05692, 1 page (2020).
Woldring, D , et al., "A Gradient of Sitewise Diversity Promotes Evolutionary Fitness for Binder Discovery in a Three-Helix Bundle Protein Scaffold", Biochemistry 56, 1656-1671 (2017).

* cited by examiner

*Primary Examiner* — Sudhakar Katakam
*Assistant Examiner* — Zachary J Miknis
(74) *Attorney, Agent, or Firm* — Viksnins Harris Padys Malen LLP

(57) ABSTRACT

Certain embodiments of the invention provide helix sequences that have affinity for Death Receptor 5 (DR5). Certain embodiments of the invention provide an isolated anti-DR5 polypeptide (e.g., affibody for DR5) that modulates the activity and/or conformation of DR5. Certain embodiments of the invention provide methods of noncompetitively inhibiting DR5 and/or treating a fatty liver disorder.

20 Claims, 8 Drawing Sheets

Specification includes a Sequence Listing.

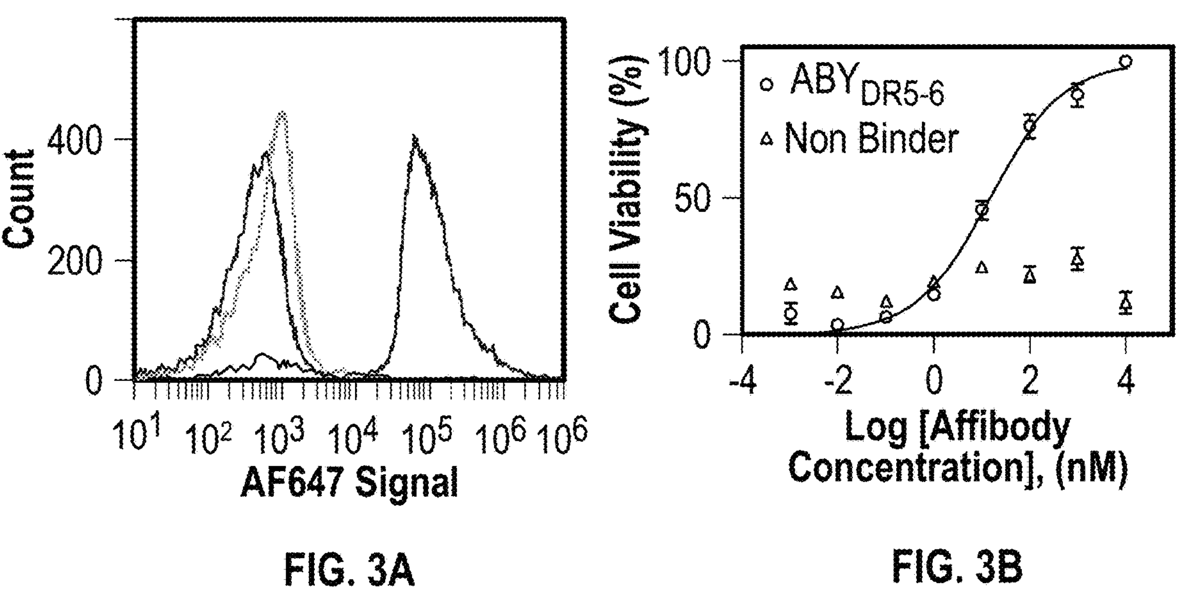
FIG. 3A
FIG. 3B
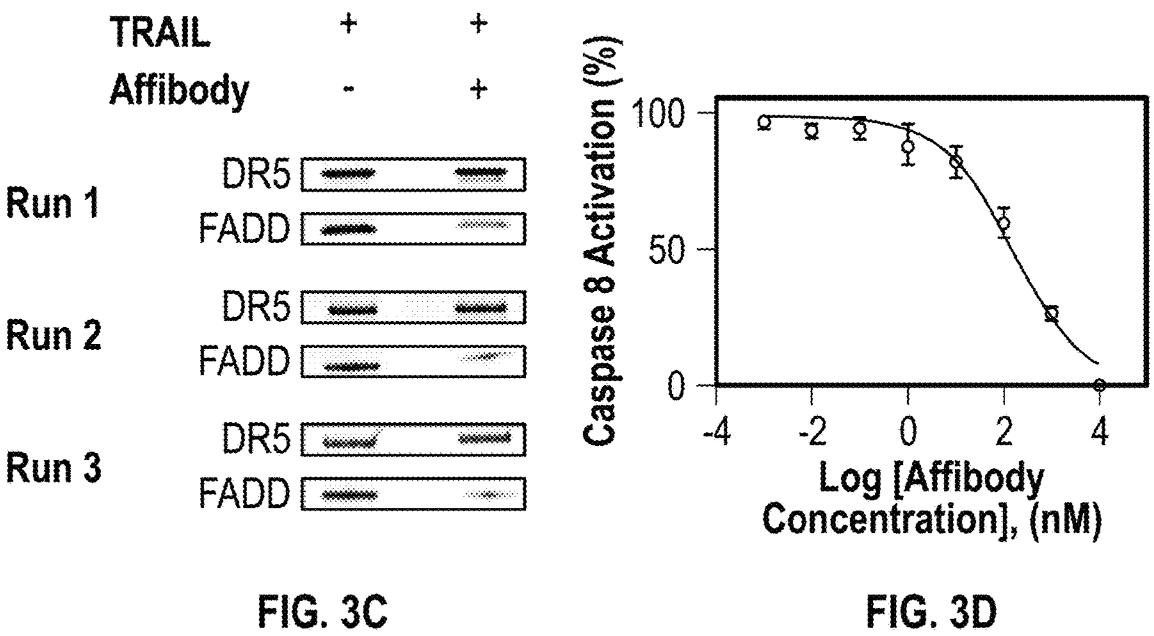
FIG. 3C
FIG. 3D

ANTI-DR5 POLYPEPTIDES AND METHODS OF USE THEREOF

CROSS REFERENCE TO RELATED APPLICATION

This application claims priority to U.S. Provisional Application No. 62/985,105 filed on 4 Mar. 2020, which is incorporated by reference herein.

GOVERNMENT FUNDING

This invention was made with government support under EB023339, DK041876, A1144932 and GM131814 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 15, 2021, is named 09531-506W01_SL.txt and is 14,503 bytes in size.

BACKGROUND OF THE INVENTION

Tumor necrosis factor (TNF) ligands and TNF receptors (TNFR) are essential modulators of the immune response and are critically involved in organ development and tissue homeostasis. Activation of the TNFR members via their cognate ligands effects cell proliferation, survival, and apoptosis. Excessive or impaired cell death is associated with pathophysiology of several acute and chronic diseases, including developmental, autoimmune, neurodegenerative diseases, and cancer. Neutralization of TNF-α with monoclonal antibodies has significant clinical benefit in patients with rheumatoid arthritis, inflammatory bowel disease, and psoriasis. Moreover, several agonistic death receptor-specific antibodies are in various stages of clinical trials. However, the global blockade of TNF ligand causes several undesirable side effects, such as tuberculosis, pneumonia, and an increased risk of lymphomas. Recent breakthroughs regarding the structure and biophysics of TNF receptors have shifted the current therapeutic paradigm of global TNF ligand inhibition to selective targeting of the receptor itself. In particular, blocking oligomerization of TNF receptors has been considered a potential therapeutic target. Previous study showed that it is possible to inhibit TNFR signaling by specifically targeting the receptor dimer, without interrupting ligand binding. However, despite progress, these approaches and others like them have failed to discover small molecule inhibitors with even nanomolar potency. Additionally, these studies have been limited to molecules that competitively target the receptor-receptor or receptor-ligand interfaces, whereas non-competitive agents have the potential for greater efficacy. Also, protein ligands may provide larger surface area for elevated affinity and target a wider array of epitopes. Thus, there is a need for new biologic agents that modulate TNFR.

SUMMARY OF THE INVENTION

Accordingly, certain embodiments of the invention provide an isolated anti-DR5 polypeptide, comprising one or more helix domains selected from the group consisting of:

(a) a helix 1 sequence comprising an amino acid sequence having at least 80% sequence identity to an amino acid sequence of any one of SEQ ID NOs:1 to 6, or a sequence having up to 1 or 2 substitutions relative to any one of SEQ ID NOs:1 to 6; and (b) a helix 2 sequence comprising an amino acid sequence having at least 80% sequence identity to an amino acid sequence of any one of SEQ ID NOs:7 to 12, or a sequence having up to 1 or 2 substitutions relative to any one of SEQ ID NOs:7 to 12.

Certain embodiments of the invention provide an isolated anti-DR5 polypeptide, comprising one or more helix domains selected from the group consisting of:

(a) a helix 1 sequence comprising an amino acid sequence having at least 80% sequence identity to an amino acid sequence of any one of SEQ ID NOs:1 to 6; and (b) a helix 2 sequence comprising an amino acid sequence having at least 80% sequence identity to an amino acid sequence of any one of SEQ ID NOs:7 to 12.

Certain embodiments of the invention provide a composition comprising an isolated anti-DR5 polypeptide described herein, and a carrier.

Certain embodiments of the invention provide an isolated nucleic acid comprising a nucleotide sequence encoding an isolated anti-DR5 polypeptide described herein.

Certain embodiments of the invention provide a vector comprising the nucleic acid described herein.

Certain embodiments of the invention provide a cell comprising the nucleic acid or the vector described herein.

Certain embodiments of the invention provide a method of inhibiting the activity of DR5, comprising contacting DR5 with an isolated anti-DR5 polypeptide described herein.

Certain embodiments of the invention provide an isolated anti-DR5 polypeptide described herein for use in diagnosis or medical therapy.

Certain embodiments of the invention provide a method for treating a fatty liver disorder in a mammal, comprising administering an effective amount of an anti-DR5 isolated polypeptide described herein to the mammal.

Certain embodiments of the invention provide an isolated anti-DR5 polypeptide described herein for the prophylactic or therapeutic treatment of a fatty liver disorder.

Certain embodiments of the invention provide the use of an isolated anti-DR5 polypeptide described herein to prepare a medicament for the treatment of a fatty liver disorder in a mammal.

Certain embodiments of the invention provide a kit comprising an isolated anti-DR5 polypeptide described herein, packaging material, and instructions for administering the isolated polypeptide to a mammal to treat a fatty liver disorder.

BRIEF DESCRIPTION OF THE FIGURES

(FIG. 1A) Schematic of the affibody scaffold displayed on the surface of yeast. (FIG. 1B) Flow chart for the discovery and evolution of DR5 binders from the naïve ABY library. Yeast displaying the affibody population evolved for binding the extracellular domain of DR5 were labeled with mouse c-Myc antibody, followed by AF647-conjugated anti-mouse antibody as well as cellular lysate with DR5-GFP (FIG. 1C) or LAG3-GFP (FIG. 1D). Affibody display and target binding were detected by flow cytometry.

(FIG. 2A) Amino acid sequences of six clones from the evolved population against DR5 were aligned with the wild-type affibody (SEQ ID NOS 43, 29, 41, and 31-34, respectively, in order of appearance). Dashes indicate amino acids that are identical with the wild-type. (FIG. 2B) Coomassie blue staining of soluble ABY protein isolated via SDS-PAGE. Open circle represents soluble affibody. (FIG. 2C) HEK293 cells with stable expression of DR5ΔCD-GFP were incubated with 1 μM soluble $ABY_{DR5}$ variants. Binding was detected with AF647 conjugated anti-His6 antibody by flow cytometry. Leftmost main peak: HEK293 stable cells; rightmost main peak: HEK293 stable cells treated with $ABY_{DR5-6}$; central main peaks: HEK293 stable cells treated with $ABY_{DR5}$ 1-5, respectively. (FIG. 2D) Affinity titration of $ABY_{DR5-6}$. HEK293 cells with a stable expression of DR5ΔCD-GFP or TNFR1ΔCD-GFP or transient expression of LAG3-GFP were incubated with increasing concentrations of soluble $ABY_{DR5-6}$. Binding was detected by AF647-conjugated anti-Hiss antibody via flow cytometry. Data are presented as mean±standard deviation of three independent experiments. The line represents the minimization of the sum of squared errors for a 1:1 binding model.

FIGS. 3A-3D. $ABY_{DR5-6}$ inhibits TRAIL-induced apoptosis. (FIG. 3A) Jurkat cells were incubated with anti-DR5 antibody, followed by AF647-conjugated mouse secondary antibody, and analyzed by flow cytometry. Rightmost main peak: fully labeled cells; leftmost main peak: unlabeled cells; central main peak (partly overlaps with leftmost main peak): cells lacking primary DR5 antibody. (FIG. 3B) $ABY_{DR5-6}$ inhibits TRAIL-induced cell death as determined by MTT assay. Jurkat cells were treated with increasing concentrations of soluble $ABY_{DR5-6}$ (1 pM-10 μM) then stimulated with TRAIL (0.1 μg/mL; 3 nM) for 16 hours. The line represents the minimization of the sum of squared errors for a 1:1 inhibition model. Data are presented as mean±standard deviation of three independent experiments. (FIG. 3C) Effect of $ABY_{DR5-6}$ on TRAIL-induced FADD recruitment to DR5. Jurkat cells were incubated with 200 nM affibody then stimulated with FLAG-tagged TRAIL. TRAIL and associated molecules were immunoprecipitated on anti-FLAG-conjugated magnetic beads, resolved using SDS-PAGE gels, and subjected to western blotting using anti-DR5 and FADD antibodies. (FIG. 3D) Caspase-8 activity was measured in Jurkat cells treated with increasing concentrations of soluble $ABY_{DR5-6}$ (1 pM-10 μM) and TRAIL (0.1 μg/mL). The line represents the minimization of the sum of squared errors for a 1:1 inhibition model. Data are presented as mean±standard deviation of three independent experiments.

(FIG. 4A) HEK293 cells with stable expression of DR5ΔCD-GFP were incubated with TRAIL (50 nM) and TRAIL+soluble $ABY_{DR5-6}$ (200 nM). TRAIL binding was detected with rabbit anti-TRAIL antibody, followed by AF647-conjugated anti-rabbit antibody, as measured by flow cytometry. Leftmost main peak: HEK293 stable cells; Rightmost main peaks: HEK293 stable cells treated with TRAIL only; and HEK293 stable cells treated with TRAIL and $ABY_{DR5-6}$, these two treatment groups showed overlapped staining as shown in the rightmost main peaks. (FIG. 4B) TRAIL-DR5 binding was determined by a pull-down assay with anti-GFP magnetic beads. DR5ΔCD-GFP lysate was mixed with anti-GFP beads and incubated at 4° C. for 2 hours. The beads were then washed thrice to remove the unbound proteins. Soluble-TRAIL (50 nM) and TRAIL+ $ABY_{DR5-6}$ (200 nM) were added to DR5-GFP coated magnetic beads and rotated at 4° C. for 2-4 hours. Beads were washed thrice, and pulled-down proteins were resolved by SDS-PAGE and immunoblotted with anti-GFP, TRAIL and His5 antibodies.

(FIG. 6A) Huh-7 cells grown in 96-well plates were treated with recombinant human TRAIL (20 ng/mL) for 16 h in 0-10 μM $ABY_{DR5-6}$. (FIG. 6B) Huh-7 cells grown in 96-well plates were treated with palmitate (600 μM) for 16 h in 0-10 μM $ABY_{DR5-6}$. Cell death was detected with a mixture of cell-permeable Hoechst 33342 and impermeable Sytox Green DNA fluorescent dyes.

(FIG. 7A) Affinity titration of $ABY_{DR5-6}$. HEK293 cells with a stable expression of DR5ΔCD-GFP or transient expression of DR4ΔCD-GFP were incubated with increasing concentrations of soluble $ABY_{DR5-6}$ Binding was detected by AF647-conjugated anti-His5 antibody via flow cytometry. Data are presented as mean±standard deviation of three independent experiments. (FIG. 7B) $ABY_{DR5-6}$-DR4 binding was determined by a pull-down assay with anti-His magnetic beads. Soluble $ABY_{DR5-6}$ (200 nM) was mixed with anti-His beads and incubated at 4° C. for 2 hours. The beads were then washed thrice to remove the unbound proteins. Soluble-DR4-Fc (100 nM) or Soluble-DR5-Fc (100 nM) was added to $ABY_{DR5-6}$ coated magnetic beads and rotated at 4° C. for 2-4 hours. Beads were washed thrice, and pulled-down proteins were resolved by SDS-PAGE and immunoblotted with anti-DR4 and anti-DR5 antibodies. (FIG. 7C) Three runs of pull-down experiments (same methods as FIG. 7B) are shown.

DETAILED DESCRIPTION

Figures 1A, 1B, 1C, 1D:
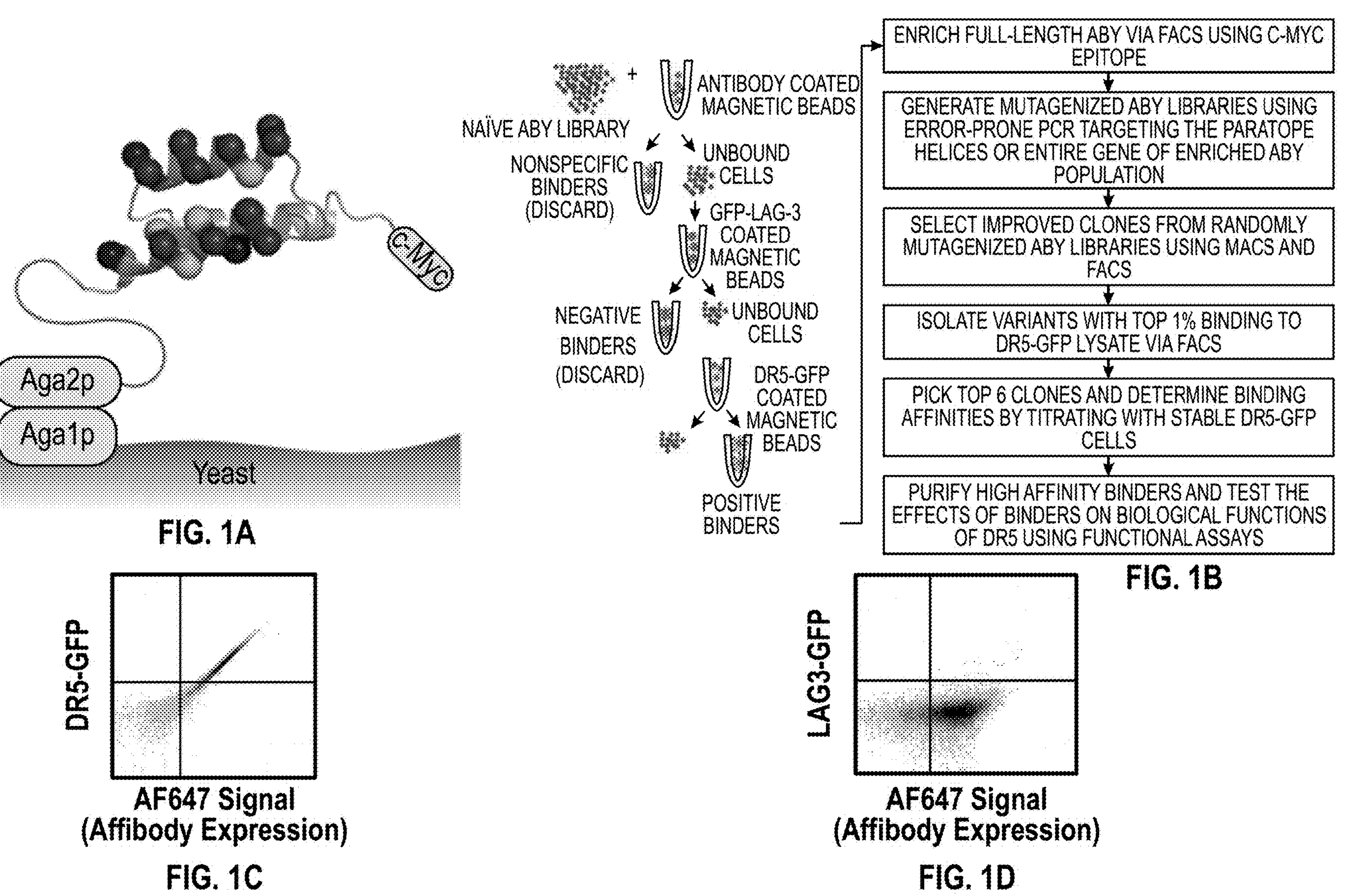
FIGS. 1A-1D. Identification and evolution of DR5-specific ABY binders using yeast surface display.

Fatty acid-induced upregulation of death receptor 5 (DR5) and its cognate ligand, tumor necrosis factor-related apoptosis-inducing ligand (TRAIL), promotes hepatocyte lipoapoptosis, which is key to fatty liver disease progression. Inhibition of DR5 (a member of TNF receptor superfamily) signaling is attractive for treating fatty liver disease. Ligand competition is prevalent in tumor necrosis factor receptor antagonism, but recent studies suggest a compelling alternative: non-competitive inhibition through perturbation of receptor conformation. As described in Example 1, a yeast-displayed combinatorial library was used to identify a synthetic affibody that specifically binds DR5. Biophysical and biochemical studies show that the affibody neither blocks TRAIL binding nor prevents receptor-receptor interaction. Live-cell fluorescence lifetime measurements indicate that the affibody induces conformational change in DR5 transmembrane dimers and favors an inactive receptor state. The affibody inhibits apoptosis in TRAIL- or palmitate-treated Huh-7 cells, an in vitro fatty liver disease model. Thus, described herein are a series of affibodies that have a unique mechanism of action and which may be useful for the treatment of fatty liver disease.

As used herein, the term “affibody” or “affibody molecule” refers to an engineered small protein ligand based on the three helical bundle Z domain of the Ig-binding region of protein A. In certain embodiments, an affibody is a small protein of about 58 amino acids in length (about 6~7 KDa), which may have a N-terminal segment, helix 1, loop 1, helix 2, loop 2, helix 3 and a C-terminal segment. Affibody molecule libraries can be constructed by randomization of about 13~17 amino acid residues in helices 1 and 2 of the three-helix bundle protein to screen for specific binders, followed by further affinity maturation for more potent binders. Thus, helix 1 and helix 2 are believed to play a role in an affibody’s binding properties towards a target. For example, Ren, et al. showed smaller 2-helix affibody derivatives have excellent binding affinity (*J Nucl Med.* 2009 September; 50(9): 1492-1499).

Additionally, affibodies or fragments thereof (e.g., binding portions of affibody), have served as a versatile fusion partner with a variety of other functional domains, such as enzymes, fluorescent proteins, toxins, antibodies or fragments thereof (e.g., Fc domain), albumin binding domains, additional identical affibodies for preparing homodimers or multimers, additional distinct affibodies for generating bi-specificity or multi-specificity, to provide a diverse range of biologic agents (may be larger than 6~7 KDa) that contain at least an affibody or a portion of an affibody.

Isolated Polypeptides Having Affinity for DR5

Thus, certain embodiments of the invention provide an isolated anti-DR5 polypeptide that comprises a helix 1 sequence and/or a helix 2 sequence, an affibody sequence or a fragment thereof, derived from any of the following affibodies described herein: $ABY_{DR5-6}$, $ABY_{DR5-5}$, $ABY_{DR5-4}$, $ABY_{DR5-3}$, $ABY_{DR5-2}$ and $ABY_{DR5-1}$. The amino acid sequences of the helix 1 and helix 2 of these DR5 binders are set forth in Table 1 below.

In certain embodiments, an isolated anti-DR5 polypeptide comprises a helix 1 as described in any of the embodiments provided herein, and/or a helix 2 as described in any of the embodiments provided herein.

Thus, certain embodiments of the invention provide an isolated anti-DR5 polypeptide, comprising one or more helix domains selected from the group consisting of:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NOs:1 to 6, or a sequence having up to 1 or 2 substitutions relative to any one of SEQ ID NOs:1 to 6; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:7 to 12, or a sequence having up to 1 or 2 substitutions relative to any one of SEQ ID NOs:7-12.

Certain embodiments of the invention provide an isolated anti-DR5 polypeptide, comprising one or more helix domains selected from the group consisting of:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:1 to 6; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:7 to 12.

In certain embodiments, the anti-DR5 polypeptide comprises one or more helix domains selected from the group consisting of:

(a) a helix 1 sequence comprising an amino acid sequence having at least 90% (e.g., 91%, 92%, 93%, 94%, 95%, 96%, 97%, 98%, 99% or 100%) sequence identity to an amino acid sequence of any one of SEQ ID NO:1 to 6; and (b) a helix 2 sequence comprising an amino acid sequence having at least 90% (e.g., 91%, 92%, 93%, 94%, 95%, 96%, 97%, 98%, 99% or 100%) sequence identity to an amino acid sequence of any one of SEQ ID NO:7 to 12.

In certain embodiments, the anti-DR5 polypeptide comprises one or more helix domains selected from the group consisting of:

(a) a helix 1 sequence comprising an amino acid sequence having up to 2 substitutions relative to any one of SEQ ID NOs:1 to 6; and (b) a helix 2 sequence comprising an amino acid sequence having up to 2 substitutions relative to any one of SEQ ID NOs:7 to 12.

In certain embodiments, the anti-DR5 polypeptide comprises one or more helix domains selected from the group consisting of:

(a) a helix 1 sequence comprising an amino acid sequence having up to 1 substitution relative to any one of SEQ ID NOs:1 to 6; and (b) a helix 2 sequence comprising an amino acid sequence having up to 1 substitution relative to any one of SEQ ID NOs:7 to 12.

In certain embodiments, the anti-DR5 polypeptide comprises one or more helix domains selected from the group consisting of:

(a) a helix 1 sequence comprising the amino acid sequence of any one of SEQ ID NO:1 to 6; and (b) a helix 2 sequence comprising the amino acid sequence of any one of SEQ ID NO:7 to 12.

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:1 to 6.

In certain embodiments, the anti-DR5 polypeptide comprises a helix 1 sequence comprising an amino acid sequence having at least 90% (e.g., 91%, 92%, 93%, 94%, 95%, 96%, 97%, 98%, 99% or 100%) sequence identity to an amino acid sequence of any one of SEQ ID NO:1 to 6.

In certain embodiments, the anti-DR5 polypeptide comprises a helix 1 sequence comprising an amino acid sequence having up to 2 substitutions relative to any one of SEQ ID NOs:1 to 6. In certain embodiments, the anti-DR5 polypeptide comprises a helix 1 sequence comprising an amino acid sequence having up to 1 substitution relative to any one of SEQ ID NOs:1 to 6.

In certain embodiments, the anti-DR5 polypeptide comprises a helix 1 sequence comprising an amino acid sequence of any one of SEQ ID NO:1 to 6.

In certain embodiments, the anti-DR5 polypeptide comprises a helix 1 sequence consisting of an amino acid sequence of any one of SEQ ID NO:1 to 6.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:7 to 12.

In certain embodiments, the anti-DR5 polypeptide comprises a helix 2 sequence comprising an amino acid sequence having at least 90% (e.g., 91%, 92%, 93%, 94%, 95%, 96%, 97%, 98%, 99% or 100%) sequence identity to an amino acid sequence of any one of SEQ ID NO:7 to 12.

In certain embodiments, the anti-DR5 polypeptide comprises a helix 2 sequence comprising an amino acid sequence having up to 2 substitutions relative to any one of SEQ ID NOs:7 to 12. In certain embodiments, the anti-DR5 polypeptide comprises a helix 2 sequence comprising an amino acid sequence having up to 1 substitution relative to any one of SEQ ID NOs:7 to 12.

In certain embodiments, the anti-DR5 polypeptide comprises a helix 2 sequence comprising an amino acid sequence of any one of SEQ ID NO:7 to 12.

In certain embodiments, the anti-DR5 polypeptide comprises a helix 2 sequence consisting of an amino acid sequence of any one of SEQ ID NO:7 to 12.

In certain embodiments, the anti-DR5 polypeptide comprises two, three, four, five, six, seven, eight, or nine helices as described herein.

In certain embodiments, the anti-DR5 polypeptide comprises two helices as described herein. In certain embodiments, the anti-DR5 polypeptide comprises a helix 1 sequence and a helix 2 sequence as described herein.

Certain embodiments provide affibodies and binding portions of affibodies that specifically bind to DR5. Thus, in some embodiments, a polypeptide described herein is an affibody, or fragment thereof, comprising: a helix 1 sequence and a helix 2 sequence.

In certain embodiments, the isolated anti-DR5 polypeptide, comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:1 to 6, or a sequence having up to 1 or 2 substitutions relative to any one of SEQ ID NOs:1 to 6; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:7 to 12, or a sequence having up to 1 or 2 substitutions relative to any one of SEQ ID NOs:7-12.

In certain embodiments, the isolated anti-DR5 polypeptide, comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:1 to 6; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NO:7 to 12.

In certain embodiments, the anti-DR5 polypeptide comprises:

(a) a helix 1 sequence comprising an amino acid sequence having at least 90% (e.g., 91%, 92%, 93%, 94%, 95%, 96%, 97%, 98%, 99% or 100%) sequence identity to an amino acid sequence of any one of SEQ ID NO:1 to 6; and (b) a helix 2 sequence comprising an amino acid sequence having at least 90% (e.g., 91%, 92%, 93%, 94%, 95%, 96%, 97%, 98%, 99% or 100%) sequence identity to an amino acid sequence of any one of SEQ ID NO:7 to 12.

In certain embodiments, the isolated anti-DR5 polypeptide, comprises:

(a) a helix 1 sequence comprising an amino acid sequence having up to 2 substitutions relative to any one of SEQ ID NOs:1 to 6; and (b) a helix 2 sequence comprising an amino acid sequence having up to 2 substitutions relative to any one of SEQ ID NOs:7-12.

In certain embodiments, the isolated anti-DR5 polypeptide, comprises:

(a) a helix 1 sequence comprising an amino acid sequence having up to 1 substitution relative to any one of SEQ ID NOs:1 to 6; and (b) a helix 2 sequence comprising an amino acid sequence having up to 1 substitution relative to any one of SEQ ID NOs:7-12.

In certain embodiments, the anti-DR5 polypeptide comprises:

(a) a helix 1 sequence comprising an amino acid sequence of any one of SEQ ID NO:1 to 6; and (b) a helix 2 sequence comprising an amino acid sequence of any one of SEQ ID NO:7 to 12.

In certain embodiments, the anti-DR5 polypeptide comprises a helix 1 sequence, a loop 1 sequence and a helix 2 sequence as described herein (e.g., as described in Table 1 below).

In certain embodiments, the polypeptide is a cyclic polypeptide (e.g., a 2-helix polypeptide may comprise helix 1, loop 1 such as SEQ ID NO:27 and helix 2, while the 2-helix polypeptide may be constrained with a disulfide bridge formed between two homocysteines at the N and C terminals of the polypeptide).

In certain embodiments, the anti-DR5 polypeptide comprises a N-terminal region, a helix 1 sequence, a loop 1 sequence and a helix 2 sequence as described herein.

In certain embodiments, the anti-DR5 polypeptide comprises three helices as described herein. Thus, in certain embodiments, the polypeptide further comprises a helix 3 sequence. In certain embodiments, the anti-DR5 polypeptide comprises a helix 3 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SEQ ID NO: 13 or 14, or a sequence having up to 1 or 2 substitutions relative to SEQ ID NO: 13 or 14. In certain embodiments, the anti-DR5 polypeptide comprises a helix 3 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of SEQ ID NO:13 or 14. In certain embodiments, the anti-DR5 polypeptide comprises a helix 3 sequence comprising an amino acid sequence having up to 1 or 2 substitutions relative to SEQ ID NO: 13 or 14. In certain embodiments, the anti-DR5 polypeptide comprises a helix 1 sequence, a helix 2 sequence and a helix 3 sequence as described herein.

In certain embodiments, a polypeptide described herein is an affibody comprising: a N-terminal region, a helix 1 sequence, a loop 1 sequence, a helix 2 sequence, a loop 2 sequence, a helix 3 sequence and a C-terminal region, as described herein (e.g., Table 1).

In certain embodiments, the anti-DR5 polypeptide comprises a loop 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NOs:17-26, or a sequence having up to 1 or 2 substitutions relative to any one of SEQ ID NO:17-26. In certain embodiments, the anti-DR5 polypeptide comprises a loop 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to an amino acid sequence of any one of SEQ ID NOs:17-26. In certain embodiments, the anti-DR5 polypeptide comprises a loop 1 sequence comprising an amino acid sequence having up to 1 or 2 substitutions relative to any one of SEQ ID NO: 17-26. In certain embodiments, the anti-DR5 polypeptide comprises a loop 1 sequence comprising an amino acid sequence of any one of SEQ ID NOs:17-26. In certain embodiments, the anti-DR5 polypeptide comprises a loop 1 sequence comprising an amino acid sequence of any one of SEQ ID NOs:17-23.

In certain embodiments, the anti-DR5 polypeptide comprises a helix 1 sequence comprising the amino acid sequence of any of one of SEQ ID NOs:1-6, a loop 1 sequence comprising an amino acid sequence of any one of SEQ ID NOs:17-26, and a helix 2 sequence comprising an amino acid sequence of any one of SEQ ID NOs:7-12.

In certain embodiments, the anti-DR5 polypeptide comprises a N-terminal sequence comprising an amino acid sequence having up to 1 or 2 substitutions relative to any one of SEQ ID NO:15, 16 or 42. In certain embodiments, the anti-DR5 polypeptide comprises a loop 2 sequence comprising an amino acid sequence having up to 1 or 2 substitutions relative to SEQ ID NO:27. In certain embodiments, the anti-DR5 polypeptide comprises a C-terminal sequence comprising an amino acid sequence having up to 1 or 2 substitutions relative to SEQ ID NO:28.

In certain embodiments, the anti-DR5 polypeptide comprises a helix 1 sequence comprising an amino acid sequence of any one of SEQ ID NOs:1-6, a loop 1 sequence comprising an amino acid sequence of any one of SEQ ID NOs:17-26, a helix 2 sequence comprising an amino acid sequence of any one of SEQ ID NOs:7-12, a loop 2 sequence comprising SEQ ID NO:27 and a helix 3 sequence comprising an amino acid sequence of any one of SEQ ID NOs:13-14.

In certain embodiments, the anti-DR5 polypeptide comprises a N-terminal sequence comprising an amino acid sequence of any one of SEQ ID NOs:15-16 and 42, a helix 1 sequence comprising an amino acid sequence of any one of SEQ ID NOs:1-6, a loop 1 sequence comprising an amino acid sequence of any one of SEQ ID NOs:17-26, a helix 2 sequence comprising an amino acid sequence of any one of SEQ ID NOs:7-12, a loop 2 sequence comprising SEQ ID NO:27, a helix 3 sequence comprising an amino acid sequence of any one of SEQ ID NOs:13-14 and a C-terminal sequence comprising SEQ ID NO:28.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to any one of SEQ ID NOs:29-34 and 41.

In certain embodiments, the anti-DR5 polypeptide comprises an amino acid sequence that has at least 90% (e.g., 91%, 92%, 93%, 94%, 95%, 96%, 97%, 98%, 99% or 100%) sequence identity to any one of SEQ ID NOs:29-34 and 41.

In certain embodiments, the anti-DR5 polypeptide comprises an amino acid sequence that has at least 95% (e.g., 96%, 97%, 98%, 99% or 100%) sequence identity to any one of SEQ ID NOs:29-34 and 41.

In certain embodiments, the anti-DR5 polypeptide comprises an amino acid sequence of any one of SEQ ID NOs:29-34 and 41.

In certain embodiments, the anti-DR5 polypeptide consists of an amino acid sequence of any one of SEQ ID NOs:29-34 and 41.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:29. In certain embodiments, the anti-DR5 polypeptide comprises an amino acid sequence that has at least 90% (e.g., 91%, 92%, 93%, 94%, 95%, 96%, 97%, 98%, 99% or 100%) sequence identity SEQ ID NO:29. In certain embodiments, the anti-DR5 polypeptide comprises an amino acid sequence that has at least 95% (e.g., 96%, 97%, 98%, 99% or 100%) sequence identity to SEQ ID NO:29. In certain embodiments, the anti-DR5 polypeptide comprises an amino acid sequence of SEQ ID NO:29. In certain embodiments, the anti-DR5 polypeptide consists of an amino acid sequence of SEQ ID NO:29.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:30. In certain embodiments, the anti-DR5 polypeptide comprises an amino acid sequence that has at least 90% (e.g., 91%, 92%, 93%, 94%, 95%, 96%, 97%, 98%, 99% or 100%) sequence identity SEQ ID NO:30. In certain embodiments, the anti-DR5 polypeptide comprises an amino acid sequence that has at least 95% (e.g., 96%, 97%, 98%, 99% or 100%) sequence identity to SEQ ID NO:30. In certain embodiments, the anti-DR5 polypeptide comprises an amino acid sequence of SEQ ID NO:30. In certain embodiments, the anti-DR5 polypeptide consists of an amino acid sequence of SEQ ID NO:30.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:41. In certain embodiments, the anti-DR5 polypeptide comprises an amino acid sequence that has at least 90% (e.g., 91%, 92%, 93%, 94%, 95%, 96%, 97%, 98%, 99% or 100%) sequence identity SEQ ID NO:41. In certain embodiments, the anti-DR5 polypeptide comprises an amino acid sequence that has at least 95% (e.g., 96%, 97%, 98%, 99% or 100%) sequence identity to SEQ ID NO:41. In certain embodiments, the anti-DR5 polypeptide comprises an amino acid sequence of SEQ ID NO:41. In certain embodiments, the anti-DR5 polypeptide consists of an amino acid sequence of SEQ ID NO:41.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:31. In certain embodiments, the anti-DR5 polypeptide comprises an amino acid sequence that has at least 90% (e.g., 91%, 92%, 93%, 94%, 95%, 96%, 97%, 98%, 99% or 100%) sequence identity SEQ ID NO:31. In certain embodiments, the anti-DR5 polypeptide comprises an amino acid sequence that has at least 95% (e.g., 96%, 97%, 98%, 99% or 100%) sequence identity to SEQ ID NO:31. In certain embodiments, the anti-DR5 polypeptide comprises an amino acid sequence of SEQ ID NO:31. In certain embodiments, the anti-DR5 polypeptide consists of an amino acid sequence of SEQ ID NO:31.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:32. In certain embodiments, the anti-DR5 polypeptide comprises an amino acid sequence that has at least 90% (e.g., 91%, 92%, 93%, 94%, 95%, 96%, 97%, 98%, 99% or 100%) sequence identity SEQ ID NO:32. In certain embodiments, the anti-DR5 polypeptide comprises an amino acid sequence that has at least 95% (e.g., 96%, 97%, 98%, 99% or 100%) sequence identity to SEQ ID NO:32. In certain embodiments, the anti-DR5 polypeptide comprises an amino acid sequence of SEQ ID NO:32. In certain embodiments, the anti-DR5 polypeptide consists of an amino acid sequence of SEQ ID NO:32.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:33. In certain embodiments, the anti-DR5 polypeptide comprises an amino acid sequence that has at least 90% (e.g., 91%, 92%, 93%, 94%, 95%, 96%, 97%, 98%, 99% or 100%) sequence identity SEQ ID NO:33. In certain embodiments, the anti-DR5 polypeptide comprises an amino acid sequence that has at least 95% (e.g., 96%, 97%, 98%, 99% or 100%) sequence identity to SEQ ID NO:33. In certain embodiments, the anti-DR5 polypeptide comprises an amino acid sequence of SEQ ID NO:33. In certain embodiments, the anti-DR5 polypeptide consists of an amino acid sequence of SEQ ID NO:33.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:34. In certain embodiments, the anti-DR5 polypeptide comprises an amino acid sequence that has at least 90% (e.g., 91%, 92%, 93%, 94%, 95%, 96%, 97%, 98%, 99% or 100%) sequence identity to SEQ ID NO:34. In certain embodiments, the anti-DR5 polypeptide comprises an amino acid sequence that has at least 95% (e.g., 96%, 97%, 98%, 99% or 100%) sequence identity to SEQ ID NO:34. In certain embodiments, the anti-DR5 polypeptide comprises an amino acid sequence of SEQ ID NO:34. In certain embodiments, the anti-DR5 polypeptide consists of an amino acid sequence of SEQ ID NO:34.

In certain embodiments, the anti-DR5 polypeptide comprises homo or hetero multimer of an affibody as described herein, or a fragment thereof. In certain embodiments, the polypeptide comprises two affibodies or two fragments thereof. In certain embodiments, the anti-DR5 polypeptide comprises four helices as described above. In certain embodiments, the anti-DR5 polypeptide comprises two helix 1 sequences (e.g., same or different helix 1) and two helix 2 sequences (e.g., same or different helix 2) as described herein.

In certain embodiments, the anti-DR5 polypeptide comprises six helices as described above. In certain embodiments, the anti-DR5 polypeptide comprises three helix 1 sequences and three helix 2 sequences as described above. In certain embodiments, the anti-DR5 polypeptide comprises two helix 1 sequences, two helix 2 sequences and two helix 3 sequences as described herein.

In certain embodiments, the anti-DR5 polypeptide is about 25, 50, 75, 100, 150, 200, 300, 400, 500, 600, 700, 800, 900, 1000, 1100, 1200, 1300, 1400, 1500, 1600, 1700, 1800, or 1900 amino acids in length. In certain embodiments, the anti-DR5 polypeptide is about 25 to 1900, 30 to 1800, 40 to 1700, 50 to 1600, 55 to 1500, 56 to 1400, 57 to 1300, 58 to 1200, 75 to 1100, 100 to 1000, 150 to 900, or 200 to 800 amino acids in length. In certain embodiments, the anti-DR5 polypeptide is about 45 to about 70 amino acids in length, or about 50 to about 65 amino acids in length, about 53 to about 63 amino acids in length.

In certain embodiments, the anti-DR5 polypeptide is about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids in length. In certain embodiments, the anti-DR5 polypeptide is a non-immunoglobulin polypeptide. For example, the anti-DR5 polypeptide is an affibody that is about 58 amino acid residues in length and/or about 6~7 KDa in size. In certain embodiments, the anti-DR5 polypeptide is a 2-helix affibody derivative that is about 32~38 amino acid residues (e.g., 35 aa) in length.

TABLE 1

| SEQ ID NO: | SEQUENCE | DESCRIPTION |
|---|---|---|
| | Sequences | |
| 1 | EQGYAGREIRL | Helix 1 |
| 2 | EKLDAYPVIED | Helix 1 |
| 3 | EREFAVLEISL | Helix 1 |
| 4 | EGEVAGAEITV | Helix 1 |
| 5 | ESTLAEIEILR | Helix 1 |
| 6 | EDYLAVVEIVG | Helix 1 |
| 7 | PQGGAFIGALAD | Helix 2 |
| 8 | EQVMAFIVALEN | Helix 2 |
| 9 | VQSLAFIPALGD | Helix 2 |
| 10 | GQAGAFIQALLD | Helix 2 |
| 11 | AQIYAFILALTD | Helix 2 |
| 12 | GOTLAFIFALGD | Helix 2 |
| 13 | SELLSEAKKINDS | Helix 3 |
| 14 | ANLLAEAKKLNDA | Helix 3 |
| 15 | AEAKYAK | N-terminal region example 1 |
| 16 | VDNKFNK | N-terminal region example 2 |
| 17 | LPNLTN | Loop 1 |
| 18 | LPNLTR | Loop 1 |
| 19 | LPNLTL | Loop 1 |
| 20 | LPNLTD | Loop 1 |
| 21 | LPNLTC | Loop 1 |
| 22 | LPNLNE | Loop 1 |
| 23 | LPNLNW | Loop 1 |
| 24 | LPNLNV | Loop 1 |
| 25 | LPNLNN | Loop 1 |
| 26 | DPNLNN | Loop 1 |
| 27 | DPSQS | Loop 2 |
| 28 | QAPK | C-terminal region 1 |
| 29 | AEAKYAKEQGYAGREIRLLPNLTRPQGGAFIGALADDPSQSS ELLSEAKKINDSQAPK | $ABY_{DR5-1}$ |
| 30 | AEAKYAKEKLDAYPVIEDLPNLTLEQVMAFIVALENDPSQSS ELLSEAKKINDSQAPK | $ABY_{DR5-2}$, *embodiment* |
| 31 | AEAKYAKEREFAVLEISLLPNLTDVQSLAFIPALGDDPSQSS ELLSEAKKLNDSQAPK | $ABY_{DR5-3}$ |
| 32 | AEAKYAKEGEVAGAEITVLPNLTCGQAGAFIQALLDDPSQSS ELLSEAKKINDSQAPK | $ABY_{DR5-4}$ |
| 33 | AEAKYAKESTLAEIEILRLPNLTNAQIYAFILALTDDPSQSS ELLSEAKKLNDSQAPK | $ABY_{DR5-5}$ |

TABLE 1-continued

| Sequences | | |
|---|---|---|
| SEQ ID NO: | SEQUENCE | DESCRIPTION |
| 34 | AEAKYAKEDYLAVVEIVGLPNLTLGQTLAFIFALGDDPSQSS ELLSEAKKINDSQAPK | $ABY_{DR5-6}$ |
| 35 | GCCGAAGCAAAATACGCTAAAGAACAGGGGTATGCGGGGCGT GAAATCAGGCTGCTGCCGAACCTGACCCGGCCTCAGGGGGGT GCATTCATAGGGGCACTGGCTGATGACCCGTCCCAGAGCTCT GAACTCCTGTCTGAGGCGAAGAAACTGAACGATTCCCAAGCA CCAAAA | One exemplary nucleic acid sequence encoding $ABY_{DR5-1}$ |
| 36 | GCCGAAGCAAAATACAACAAAGAAAAGTTGGACGCGTACCCC GTGATCGAGGACCTGCCGAACCTGACCCTCGAGCAGGTGATG GCATTCATCGTGGCACTGGAGAACGACCCGTCCCAGAGCTCT GAACTCCTGTCTGAGGCGAAGAAACTGAACGATTCCCAAGCA CCAAAA | One exemplary nucleic acid sequence encoding $ABY_{DR5-2}$ |
| 37 | GCCGAAGCGAAATACGCTAAAGAACGGGAGTTTGCGGTTTTG GAAATCAGTTTGCTGCCGAACCTGACCGATGTGCAGAGTTTG GCATTCATACCTGCACTGGGTGATGACCCGTCCCAGAGCTCT GAACTCCTGTCTGAGGCGAAGAAACTGAACGATTCCCAAGCA CCAAAA | One exemplary nucleic acid sequence encoding $ABY_{DR5-3}$ |
| 38 | GCCGAAGCGAAATACGCTAAAGAAGGGGAGGTGGCGGGGGCG GAAATCACGGTTCTGCCGAACCTGACCTGTGGGCAGGCGGGG GCATTCATACAGGCACTGCTGGATGACCCGTCCCAGAGCTCT GAACTCCTGTCTGAGGCGAAGAAACTGAACGATTCCCAAGCA CCAAAG | One exemplary nucleic acid sequence encoding $ABY_{DR5-4}$ |
| 39 | GCCGAAGCAAAATACGCTAAAGAATCTACGTTGGCGGAGATT GAAATCCTGCGTCTGCCGAACCTGACCAATGCGCAGATTTAT GCATTCATACTTGCACTGACTGATGACCCGTCCCAGAGCTCT GAACTCCTGTCTGAGGCGAAGAAACTGAACGATTCCCAAGCA CCAAAA | One exemplary nucleic acid sequence encoding $ABY_{DR5-5}$ |
| 40 | GCCGAAGCAAAATACGCTAAAGAAGATTATTTGGCGGTGGTG GAAATCGTGGGGCTGCCGAACCTGACCCTTGGTCAGACTCTG GCATTCATATTTGCACTGGGTGATGACCCGTCCCAGAGCTCT GAACTCCTGTCTGAGGCGAAGAAACTGAACGATTCCCAAGCA CCAAAA | One exemplary nucleic acid sequence encoding $ABY_{DR5-6}$ |
| 41 | AEAKYNKEKLDAYPVIEDLPNLTLEQVMAFIVALENDPSQSS ELLSEAKKLNDSQAPK | $ABY_{DR5-2}$ |
| 42 | AEAKYNK | N-terminal region example 3 |

In certain embodiments, an anti-DR5 polypeptide as described herein recognizes one or more epitopes within DR5 (e.g., human DR5). For example, a polypeptide described herein binds one or more epitopes of the extracellular domain of DR5.

In certain embodiments, an isolated anti-DR5 polypeptide is an inhibitor of DR5. In certain embodiments, an isolated polypeptide does not block the binding between DR5 and its endogenous ligand (e.g., TRAIL). Hence, in certain embodiments, an isolated anti-DR5 polypeptide is a non-competitive inhibitor of DR5. In certain embodiments, an isolated anti-DR5 polypeptide is a specific and/or selective inhibitor of DR5. For example, a polypeptide described herein is a selective inhibitor of DR5 over DR4 or TNFR1.

In certain embodiments, an isolated polypeptide described herein triggers a conformational change of DR5 into inactive conformation.

In certain embodiments, an isolated anti-DR5 polypeptide is capable of inhibiting the activity of DR5. For example, in the presence of an anti-DR5 polypeptide described herein, the TRAIL-induced recruitment of Fas-associated death domain (FADD) is inhibited; the TRAIL-induced activation of caspase-8 is inhibited; the TRAIL-induced and/or DR5-mediated apoptosis is inhibited; as compared to a control or in the absence of an anti-DR5 polypeptide as described herein.

In certain embodiments, an isolated polypeptide described herein is capable of inhibiting hepatocyte cytotoxicity and fibrosis. In certain embodiments, an isolated polypeptide described herein is capable of inhibiting the DR5 mediated hepatocyte cytotoxicity. In certain embodiments, an isolated polypeptide described herein is capable of inhibiting the TRAIL-induced and/or fatty acid-induced hepatocyte cytotoxicity (e.g., hepatocyte lipoapoptosis).

In certain embodiments, the polypeptide as described herein comprises an albumin-binding domain (ABD) or albumin. For example, in certain embodiments, an anti-DR5 polypeptide as described herein is fused to an albumin-binding domain (ABD), such as albumin-binding domain B2A3 (BA) or B1A2B2A3 (BABA) from Streptococcal protein G (see, e.g., PNAS Dec. 2, 2014, 111 (48) 17110-17115; Makrides S C, et al. (1996) *J Pharmacol Exp Ther* 277(1):534-542; and *Exp Mol Med.* 2017 March; 49(3): e306, which are all incorporated by reference for all purposes). In certain embodiments, an anti-DR5 polypeptide as described herein is fused to human serum albumin.

In certain embodiments, the polypeptide as described herein comprises an immunoglobulin Fc fragment (e.g., IgG1, IgG2, IgG3, or IgG4 Fc fragment). For example, in certain embodiments, the anti-DR5 polypeptide as described herein is fused to an immunoglobulin Fc fragment (e.g., to the N terminal and/or C terminal of a IgG1, IgG2, IgG3, or IgG4 Fc fragment or engineered Ig Fc fragment). In certain embodiments, the IgG1 Fc fragment comprises an amino acid sequence that has at least 95% (e.g., 96%, 97%, 98%, 99% or 100%) sequence identity to the sequence of NCBI accession number 1T83_A. In certain embodiments, the IgG4 Fc fragment comprises an amino acid sequence that has at least 95% (e.g., 96%, 97%, 98%, 99% or 100%) sequence identity to the sequence of NCBI accession number 4D2N_A.

In certain embodiments, an anti-DR5 polypeptide as described herein is fused to a fluorescent protein (e.g., GFP or RFP). In certain embodiments, an anti-DR5 polypeptide is labeled with a fluorescent moiety (e.g., FITC, or an AlexaFluor dye).

In certain embodiments, an anti-DR5 polypeptide is labeled with a metal chelator (e.g., 1,4,7,10-tetraazacyclododecane-1,4,7,10-tetraacetic acid (DOTA)) and/or a radioisotope (e.g., $^{18}$F, $^{99}$mTc, $^{111}$In, $^{90}$Y $^{177}$Lu, $^{68}$Ga or $^{64}$Cu) for imaging or radiotherapy.

DR5 Binder $ABY_{DR5-6}$

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:6 (EDYLAVVEIVG), or a sequence having up to 1 or 2 substitutions relative to SEQ ID NO:6.

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:6 (EDYLAVVEIVG).

In certain embodiments, the anti-DR5 polypeptide comprises a helix 1 sequence comprising an amino acid sequence having at least 90% (e.g., 91%, 92%, 93%, 94%, 95%, 96%, 97%, 98%, 99% or 100%) sequence identity to SEQ ID NO:6.

In certain embodiments, the anti-DR5 polypeptide comprises a helix 1 sequence comprising an amino acid sequence having up to 2 substitutions relative to SEQ ID NO:6. In certain embodiments, the anti-DR5 polypeptide comprises a helix 1 sequence comprising an amino acid sequence having up to 1 substitution relative to SEQ ID NO:6.

In certain embodiments, the anti-DR5 polypeptide comprises a helix 1 sequence comprising SEQ ID NO:6.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:12 (GQTLAFIFALGD), or a sequence having up to 1 or 2 substitutions relative to SEQ ID NO:12.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:12 (GQTLAFIFALGD).

In certain embodiments, the anti-DR5 polypeptide comprises a helix 2 sequence comprising an amino acid sequence having at least 90% (e.g., 91%, 92%, 93%, 94%, 95%, 96%, 97%, 98%, 99% or 100%) sequence identity to SEQ ID NO:12.

In certain embodiments, the anti-DR5 polypeptide comprises a helix 2 sequence comprising an amino acid sequence having up to 2 substitutions relative to SEQ ID NO:12. In certain embodiments, the anti-DR5 polypeptide comprises a helix 2 sequence comprising an amino acid sequence having up to 1 substitution relative to SEQ ID NO: 12.

In certain embodiments, the anti-DR5 polypeptide comprises a helix 2 sequence comprising SEQ ID NO:12.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:6, or a sequence having up to 1 or 2 substitutions relative to SEQ ID NO:6; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:12, or a sequence having up to 1 or 2 substitutions relative to SEQ ID NO: 12.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:6; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:12.

In certain embodiment, the anti-DR5 polypeptide comprises:

(a) a helix 1 sequence comprising an amino acid sequence having at least 90% (e.g., 91%, 92%, 93%, 94%, 95%, 96%, 97%, 98%, 99% or 100%) sequence identity to SEQ ID NO:6; and (b) a helix 2 sequence comprising an amino acid sequence having at least 90% (e.g., 91%, 92%, 93%, 94%, 95%, 96%, 97%, 98%, 99% or 100%) sequence identity to SEQ ID NO:12.

In certain embodiments, the anti-DR5 polypeptide comprises a helix 1 sequence comprising an amino acid sequence having up to 2 substitutions relative to SEQ ID NO:6; and a helix 2 sequence comprising an amino acid sequence having up to 2 substitutions relative to SEQ ID NO:12. In certain embodiments, the anti-DR5 polypeptide comprises a helix 1 sequence comprising an amino acid sequence having up to 1 substitution relative to SEQ ID NO:6; and a helix 2 sequence comprising an amino acid sequence having up to 1 substitution relative to SEQ ID NO:12.

In certain embodiments, the anti-DR5 polypeptide comprises a helix 1 sequence comprising SEQ ID NO:6; and a helix 2 sequence comprising SEQ ID NO:12.

In certain embodiments, the anti-DR5 polypeptide comprises a helix 1 sequence consisting of SEQ ID NO:6; and a helix 2 sequence consisting of SEQ ID NO:12.

In certain embodiments, the anti-DR5 polypeptide comprises a helix 1 sequence comprising SEQ ID NO:6, a loop 1 sequence comprising SEQ ID NO:19, and a helix 2 sequence comprising SEQ ID NO:12.

In certain embodiments, the anti-DR5 polypeptide comprises a helix 1 sequence comprising SEQ ID NO:6, a loop 1 sequence comprising SEQ ID NO:19, a helix 2 sequence comprising SEQ ID NO:12, a loop 2 sequence comprising SEQ ID NO:27 and a helix 3 sequence comprising SEQ ID NO:13.

In certain embodiments, the anti-DR5 polypeptide comprises a N-terminal sequence comprising SEQ ID NO:15, a helix 1 sequence comprising SEQ ID NO:6, a loop 1 sequence comprising SEQ ID NO:19, a helix 2 sequence comprising SEQ ID NO:12, a loop 2 sequence comprising SEQ ID NO:27, a helix 3 sequence comprising SEQ ID NO:13 and a C-terminal sequence comprising SEQ ID NO:28.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:34: (AEAKYAKEDYLAVVEIVGLPNLTLGQTLAFIFALGDDPSQSSELLSEAKKLNDSQAPK).

In certain embodiments, the anti-DR5 polypeptide comprises an amino acid sequence that has at least 90% (e.g., 91%, 92%, 93%, 94%, 95%, 96%, 97%, 98%, 99% or 100%) sequence identity to SEQ ID NO:34.

In certain embodiments, the anti-DR5 polypeptide comprises an amino acid sequence that has at least 95% (e.g., 96%, 97%, 98%, 99% or 100%) sequence identity to SEQ ID NO:34.

In certain embodiments, the anti-DR5 polypeptide comprises the amino acid sequence of SEQ ID NO:34.

In certain embodiments, the anti-DR5 polypeptide consists of SEQ ID NO:34, which is from N-terminal to C-terminal.

In certain embodiments, the anti-DR5 polypeptide is encoded by a nucleic acid sequence that comprises a sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:40.

DR5 Binder $ABY_{DR5-5}$

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:5 (ESTLAEIEILR), or a sequence having up to 1 or 2 substitutions relative to SEQ ID NO:5.

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:5 (ESTLAEIEILR).

In certain embodiments, the anti-DR5 polypeptide comprises a helix 1 sequence comprising an amino acid sequence having at least 90% (e.g., 91%, 92%, 93%, 94%, 95%, 96%, 97%, 98%, 99% or 100%) sequence identity to SEQ ID NO:5.

In certain embodiments, the anti-DR5 polypeptide comprises a helix 1 sequence comprising an amino acid sequence having up to 2 substitutions relative to SEQ ID NO:5. In certain embodiments, the anti-DR5 polypeptide comprises a helix 1 sequence comprising an amino acid sequence having up to 1 substitution relative to SEQ ID NO:5.

In certain embodiments, the anti-DR5 polypeptide comprises a helix 1 sequence comprising SEQ ID NO:5.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:11 (AQIYAFILALTD), or a sequence having up to 1 or 2 substitutions relative to SEQ ID NO:11.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:11 (AQIYAFILALTD).

In certain embodiments, the anti-DR5 polypeptide comprises a helix 2 sequence comprising an amino acid sequence having at least 90% (e.g., 91%, 92%, 93%, 94%, 95%, 96%, 97%, 98%, 99% or 100%) sequence identity to SEQ ID NO:11.

In certain embodiments, the anti-DR5 polypeptide comprises a helix 2 sequence comprising an amino acid sequence having up to 2 substitutions relative to SEQ ID NO:11. In certain embodiments, the anti-DR5 polypeptide comprises a helix 2 sequence comprising an amino acid sequence having up to 1 substitution relative to SEQ ID NO: 11.

In certain embodiments, the anti-DR5 polypeptide comprises a helix 2 sequence comprising SEQ ID NO:11.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:5, or a sequence having up to 1 or 2 substitutions relative to SEQ ID NO:5; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:11, or a sequence having up to 1 or 2 substitutions relative to SEQ ID NO: 11.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:5; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:11.

In certain embodiments, the anti-DR5 polypeptide comprises:

(a) a helix 1 sequence comprising an amino acid sequence having at least 90% (e.g., 91%, 92%, 93%, 94%, 95%, 96%, 97%, 98%, 99% or 100%) sequence identity to SEQ ID NO:5; and (b) a helix 2 sequence comprising an amino acid sequence having at least 90% (e.g., 91%, 92%, 93%, 94%, 95%, 96%, 97%, 98%, 99% or 100%) sequence identity to SEQ ID NO:11.

In certain embodiments, the anti-DR5 polypeptide comprises a helix 1 sequence comprising an amino acid sequence having up to 2 substitutions relative to SEQ ID NO:5; and a helix 2 sequence comprising an amino acid sequence having up to 2 substitutions relative to SEQ ID NO:11. In certain embodiments, the anti-DR5 polypeptide comprises a helix 1 sequence comprising an amino acid sequence having up to 1 substitution relative to SEQ ID NO:5; and a helix 2 sequence comprising an amino acid sequence having up to 1 substitution relative to SEQ ID NO:11.

In certain embodiments, the anti-DR5 polypeptide comprises a helix 1 sequence comprising SEQ ID NO:5; and a helix 2 sequence comprising SEQ ID NO:11.

In certain embodiments, the anti-DR5 polypeptide comprises a helix 1 sequence consisting of SEQ ID NO:5; and a helix 2 sequence consisting of SEQ ID NO:11.

In certain embodiments, the anti-DR5 polypeptide comprises a helix 1 sequence comprising SEQ ID NO:5, a loop 1 sequence comprising SEQ ID NO:17, and a helix 2 sequence comprising SEQ ID NO:11.

In certain embodiments, the anti-DR5 polypeptide comprises a helix 1 sequence comprising SEQ ID NO:5, a loop 1 sequence comprising SEQ ID NO:17, a helix 2 sequence comprising SEQ ID NO:11, a loop 2 sequence comprising SEQ ID NO:27 and a helix 3 sequence comprising SEQ ID NO:13.

In certain embodiments, the anti-DR5 polypeptide comprises a N-terminal sequence comprising SEQ ID NO:15, a helix 1 sequence comprising SEQ ID NO:5, a loop 1 sequence comprising SEQ ID NO:17, a helix 2 sequence comprising SEQ ID NO:11, a loop 2 sequence comprising SEQ ID NO:27, a helix 3 sequence comprising SEQ ID NO:13 and a C-terminal sequence comprising SEQ ID NO:28.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:33: (AEAKYAKESTLAEIEILRLPNLTNAQIYAFILALTDDPSQSSELLSEAKKLNDSQAPK).

In certain embodiments, the anti-DR5 polypeptide comprises an amino acid sequence that has at least 90% (e.g., 91%, 92%, 93%, 94%, 95%, 96%, 97%, 98%, 99% or 100%) sequence identity to SEQ ID NO:33.

In certain embodiments, the anti-DR5 polypeptide comprises an amino acid sequence that has at least 95% (e.g., 96%, 97%, 98%, 99% or 100%) sequence identity to SEQ ID NO:33.

In certain embodiments, the anti-DR5 polypeptide comprises SEQ ID NO:33.

In certain embodiments, the anti-DR5 polypeptide consists of SEQ ID NO:33, which is from N-terminal to C-terminal.

In certain embodiments, the anti-DR5 polypeptide is encoded by a nucleic acid sequence that comprises a sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:39.

DR5 Binder ABYDR$_{5-4}$

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:4 (EGEVAGAEITV), or a sequence having up to 1 or 2 substitutions relative to SEQ ID NO:4.

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:4 (EGEVAGAEITV).

In certain embodiments, the anti-DR5 polypeptide comprises a helix 1 sequence comprising an amino acid sequence having at least 90% (e.g., 91%, 92%, 93%, 94%, 95%, 96%, 97%, 98%, 99% or 100%) sequence identity to SEQ ID NO:4.

In certain embodiments, the anti-DR5 polypeptide comprises a helix 1 sequence comprising an amino acid sequence having up to 2 substitutions relative to SEQ ID NO:4. In certain embodiments, the anti-DR5 polypeptide comprises a helix 1 sequence comprising an amino acid sequence having up to 1 substitution relative to SEQ ID NO:4.

In certain embodiments, the anti-DR5 polypeptide comprises a helix 1 sequence comprising SEQ ID NO:4.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:10 (GQAGAFIQALLD), or a sequence having up to 1 or 2 substitutions relative to SEQ ID NO:10.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:10 (GQAGAFIQALLD).

In certain embodiments, the anti-DR5 polypeptide comprises a helix 2 sequence comprising an amino acid sequence having at least 90% (e.g., 91%, 92%, 93%, 94%, 95%, 96%, 97%, 98%, 99% or 100%) sequence identity to SEQ ID NO:10.

In certain embodiments, the anti-DR5 polypeptide comprises a helix 2 sequence having up to 2 substitutions relative to SEQ ID NO:10. In certain embodiments, the anti-DR5 polypeptide comprises a helix 2 sequence having up to 1 substitution relative to SEQ ID NO:10.

In certain embodiments, the anti-DR5 polypeptide comprises a helix 2 sequence comprising SEQ ID NO:10.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:4, or a sequence having up to 1 or 2 substitutions relative to SEQ ID NO:4; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:10, or a sequence having up to 1 or 2 substitutions relative to SEQ ID NO: 10.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:4; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:10.

In certain embodiments, the anti-DR5 polypeptide comprises:

(a) a helix 1 sequence comprising an amino acid sequence having at least 90% (e.g., 91%, 92%, 93%, 94%, 95%, 96%, 97%, 98%, 99% or 100%) sequence identity to SEQ ID NO:4; and (b) a helix 2 sequence comprising an amino acid sequence having at least 90% (e.g., 91%, 92%, 93%, 94%, 95%, 96%, 97%, 98%, 99% or 100%) sequence identity to SEQ ID NO:10.

In certain embodiments, the anti-DR5 polypeptide comprises a helix 1 sequence comprising an amino acid sequence having up to 2 substitutions relative to SEQ ID NO:4; and a helix 2 sequence comprising an amino acid sequence having up to 2 substitutions relative to SEQ ID NO:10. In certain embodiments, the anti-DR5 polypeptide comprises a helix 1 sequence comprising an amino acid sequence having up to 1 substitution relative to SEQ ID NO:4; and a helix 2 sequence comprising an amino acid sequence having up to 1 substitution relative to SEQ ID NO:10.

In certain embodiments, the anti-DR5 polypeptide comprises a helix 1 sequence comprising SEQ ID NO:4; and a helix 2 sequence comprising SEQ ID NO:10.

In certain embodiments, the anti-DR5 polypeptide comprises a helix 1 sequence consisting of SEQ ID NO:4; and a helix 2 sequence consisting of SEQ ID NO:10.

In certain embodiments, the anti-DR5 polypeptide comprises a helix 1 sequence comprising SEQ ID NO:4, a loop 1 sequence comprising SEQ ID NO:21, and a helix 2 sequence comprising SEQ ID NO:10.

In certain embodiments, the anti-DR5 polypeptide comprises a helix 1 sequence comprising SEQ ID NO:4, a loop 1 sequence comprising SEQ ID NO:21, a helix 2 sequence comprising SEQ ID NO:10, a loop 2 sequence comprising SEQ ID NO:27 and a helix 3 sequence comprising SEQ ID NO:13.

In certain embodiments, the anti-DR5 polypeptide comprises a N-terminal sequence comprising SEQ ID NO:15, a helix 1 sequence comprising SEQ ID NO:4, a loop 1 sequence comprising SEQ ID NO:21, a helix 2 sequence comprising SEQ ID NO:10, a loop 2 sequence comprising SEQ ID NO:27, a helix 3 sequence comprising SEQ ID NO:13 and a C-terminal sequence comprising SEQ ID NO:28.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:32: (AEAKYAKEGEVAGAEITVLPNLTCGQAGAFIQALLDDPSQSSELLSEAKKLNDSQAPK).

In certain embodiments, the anti-DR5 polypeptide comprises an amino acid sequence that has at least 90% (e.g., 91%, 92%, 93%, 94%, 95%, 96%, 97%, 98%, 99% or 100%) sequence identity to SEQ ID NO:32.

In certain embodiments, the anti-DR5 polypeptide comprises an amino acid sequence that has at least 95% (e.g., 96%, 97%, 98%, 99% or 100%) sequence identity to SEQ ID NO:32.

In certain embodiments, the anti-DR5 polypeptide comprises SEQ ID NO:32.

In certain embodiments, the anti-DR5 polypeptide consists of SEQ ID NO:32, which is from N-terminal to C-terminal.

In certain embodiments, the anti-DR5 polypeptide is encoded by a nucleic acid sequence that comprises a sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:38.

DR5 Binder $ABY_{DR5-3}$

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:3 (EREFAVLEISL), or a sequence having up to 1 or 2 substitutions relative to SEQ ID NO:3.

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:3 (EREFAVLEISL).

In certain embodiments, the anti-DR5 polypeptide comprises a helix 1 sequence comprising an amino acid sequence having at least 90% (e.g., 91%, 92%, 93%, 94%, 95%, 96%, 97%, 98%, 99% or 100%) sequence identity to SEQ ID NO:3.

In certain embodiments, the anti-DR5 polypeptide comprises a helix 1 sequence comprising an amino acid sequence having up to 2 substitutions relative to SEQ ID NO:3. In certain embodiments, the anti-DR5 polypeptide comprises a helix 1 sequence comprising an amino acid sequence having up to 1 substitution relative to SEQ ID NO:3.

In certain embodiments, the anti-DR5 polypeptide comprises a helix 1 sequence comprising SEQ ID NO:3.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:9 (VQSLAFIPALGD), or a sequence having up to 1 or 2 substitutions relative to SEQ ID NO:9.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:9 (VQSLAFIPALGD).

In certain embodiments, the anti-DR5 polypeptide comprises a helix 2 sequence comprising an amino acid sequence having at least 90% (e.g., 91%, 92%, 93%, 94%, 95%, 96%, 97%, 98%, 99% or 100%) sequence identity to SEQ ID NO:9.

In certain embodiments, the anti-DR5 polypeptide comprises a helix 2 sequence comprising an amino acid sequence having up to 2 substitutions relative to SEQ ID NO:9. In certain embodiments, the anti-DR5 polypeptide comprises a helix 2 sequence comprising an amino acid sequence having up to 1 substitution relative to SEQ ID NO:9.

In certain embodiments, the anti-DR5 polypeptide comprises a helix 2 sequence comprising SEQ ID NO:9.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:3, or a sequence having up to 1 or 2 substitutions relative to SEQ ID NO:3; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:9, or a sequence having up to 1 or 2 substitutions relative to SEQ ID NO:9.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:3; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:9.

In certain embodiments, the anti-DR5 polypeptide comprises:

(a) a helix 1 sequence comprising an amino acid sequence having at least 90% (e.g., 91%, 92%, 93%, 94%, 95%, 96%, 97%, 98%, 99% or 100%) sequence identity to SEQ ID NO:3; and (b) a helix 2 sequence comprising an amino acid sequence having at least 90% (e.g., 91%, 92%, 93%, 94%, 95%, 96%, 97%, 98%, 99% or 100%) sequence identity to SEQ ID NO:9.

In certain embodiments, the anti-DR5 polypeptide comprises a helix 1 sequence comprising an amino acid sequence having up to 2 substitutions relative to SEQ ID NO:3; and a helix 2 sequence comprising an amino acid sequence having up to 2 substitutions relative to SEQ ID NO:9. In certain embodiments, the anti-DR5 polypeptide comprises a helix 1 sequence comprising an amino acid sequence having up to 1 substitution relative to SEQ ID NO:3; and a helix 2 sequence comprising an amino acid sequence having up to 1 substitution relative to SEQ ID NO:9.

In certain embodiments, the anti-DR5 polypeptide comprises a helix 1 sequence comprising SEQ ID NO:3; and a helix 2 sequence comprising SEQ ID NO:9.

In certain embodiments, the anti-DR5 polypeptide comprises a helix 1 sequence consisting of SEQ ID NO:3; and a helix 2 sequence consisting of SEQ ID NO:9.

In certain embodiments, the anti-DR5 polypeptide comprises a helix 1 sequence comprising SEQ ID NO:3, a loop 1 sequence comprising SEQ ID NO:20, and a helix 2 sequence comprising SEQ ID NO:9.

In certain embodiments, the anti-DR5 polypeptide comprises a helix 1 sequence comprising SEQ ID NO:3, a loop 1 sequence comprising SEQ ID NO:20, a helix 2 sequence comprising SEQ ID NO:9, a loop 2 sequence comprising SEQ ID NO:27 and a helix 3 sequence comprising SEQ ID NO:13.

In certain embodiments, the anti-DR5 polypeptide comprises a N-terminal sequence comprising SEQ ID NO:15, a helix 1 sequence comprising SEQ ID NO:3, a loop 1 sequence comprising SEQ ID NO:20, a helix 2 sequence comprising SEQ ID NO:9, a loop 2 sequence comprising SEQ ID NO:27, a helix 3 sequence comprising SEQ ID NO:13 and a C-terminal sequence comprising SEQ ID NO:28.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:31: (AEAKYAKEREFAVLEIS-LLPNLTDVQSLAFIPALGDDPSQSSELL-SEAKKLNDSQAPK).

In certain embodiments, the anti-DR5 polypeptide comprises an amino acid sequence that has at least 90% (e.g., 91%, 92%, 93%, 94%, 95%, 96%, 97%, 98%, 99% or 100%) sequence identity to SEQ ID NO:31.

In certain embodiments, the anti-DR5 polypeptide comprises an amino acid sequence that has at least 95% (e.g., 96%, 97%, 98%, 99% or 100%) sequence identity to SEQ ID NO:31.

In certain embodiments, the anti-DR5 polypeptide comprises SEQ ID NO:31.

In certain embodiments, the anti-DR5 polypeptide consists of SEQ ID NO:31, which is from N-terminal to C-terminal.

In certain embodiments, the anti-DR5 polypeptide is encoded by a nucleic acid sequence that comprises a sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:37.

DR5 Binder $ABY_{DR5\text{-}2}$

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:2 (EKLDAYPVIED), or a sequence having up to 1 or 2 substitutions relative to SEQ ID NO:2.

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:2 (EKLDAYPVIED).

In certain embodiments, the anti-DR5 polypeptide comprises a helix 1 sequence comprising an amino acid sequence having at least 90% (e.g., 91%, 92%, 93%, 94%, 95%, 96%, 97%, 98%, 99% or 100%) sequence identity to SEQ ID NO:2.

In certain embodiments, the anti-DR5 polypeptide comprises a helix 1 sequence comprising an amino acid sequence having up to 2 substitutions relative to SEQ ID NO:2. In certain embodiments, the anti-DR5 polypeptide comprises a helix 1 sequence comprising an amino acid sequence having up to 1 substitution relative to SEQ ID NO:2.

In certain embodiments, the anti-DR5 polypeptide comprises a helix 1 sequence comprising SEQ ID NO:2.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:8 (EQVMAFIVALEN), or a sequence having up to 1 or 2 substitutions relative to SEQ ID NO:8.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:8 (EQVMAFIVALEN).

In certain embodiments, the anti-DR5 polypeptide comprises a helix 2 sequence comprising an amino acid sequence having at least 90% (e.g., 91%, 92%, 93%, 94%, 95%, 96%, 97%, 98%, 99% or 100%) sequence identity to SEQ ID NO:8.

In certain embodiments, the anti-DR5 polypeptide comprises a helix 2 sequence comprising an amino acid sequence having up to 2 substitutions relative to SEQ ID NO:8. In certain embodiments, the anti-DR5 polypeptide comprises a helix 2 sequence comprising an amino acid sequence having up to 1 substitution relative to SEQ ID NO:8.

In certain embodiments, the anti-DR5 polypeptide comprises a helix 2 sequence comprising SEQ ID NO:8.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:2, or a sequence having up to 1 or 2 substitutions relative to SEQ ID NO:2; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:8, or a sequence having up to 1 or 2 substitutions relative to SEQ ID NO:8.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:2; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:8.

In certain embodiments, the anti-DR5 polypeptide comprises:

(a) a helix 1 sequence comprising an amino acid sequence having at least 90% (e.g., 91%, 92%, 93%, 94%, 95%, 96%, 97%, 98%, 99% or 100%) sequence identity to SEQ ID NO:2; and (b) a helix 2 sequence comprising an amino acid sequence having at least 90% (e.g., 91%, 92%, 93%, 94%, 95%, 96%, 97%, 98%, 99% or 100%) sequence identity to SEQ ID NO:8.

In certain embodiments, the anti-DR5 polypeptide comprises a helix 1 sequence comprising an amino acid sequence having up to 2 substitutions relative to SEQ ID NO:2; and a helix 2 sequence comprising an amino acid sequence having up to 2 substitutions relative to SEQ ID NO:8. In certain embodiments, the anti-DR5 polypeptide comprises a helix 1 sequence comprising an amino acid sequence having up to 1 substitution relative to SEQ ID NO:2; and a helix 2 sequence comprising an amino acid sequence having up to 1 substitution relative to SEQ ID NO:8.

In certain embodiments, the anti-DR5 polypeptide comprises a helix 1 sequence comprising SEQ ID NO:2; and a helix 2 sequence comprising SEQ ID NO:8.

In certain embodiments, the anti-DR5 polypeptide comprises a helix 1 sequence consisting of SEQ ID NO:2; and a helix 2 sequence consisting of SEQ ID NO:8.

In certain embodiments, the anti-DR5 polypeptide comprises a helix 1 sequence comprising SEQ ID NO:2, a loop 1 sequence comprising SEQ ID NO:19, and a helix 2 sequence comprising SEQ ID NO:8.

In certain embodiments, the anti-DR5 polypeptide comprises a helix 1 sequence comprising SEQ ID NO:2, a loop 1 sequence comprising SEQ ID NO:19, a helix 2 sequence comprising SEQ ID NO:8, a loop 2 sequence comprising SEQ ID NO:27 and a helix 3 sequence comprising SEQ ID NO:13.

In certain embodiments, the anti-DR5 polypeptide comprises a N-terminal sequence comprising SEQ ID NO:15 or 42, a helix 1 sequence comprising SEQ ID NO:2, a loop 1 sequence comprising SEQ ID NO:19, a helix 2 sequence comprising SEQ ID NO:8, a loop 2 sequence comprising SEQ ID NO:27, a helix 3 sequence comprising SEQ ID NO:13 and a C-terminal sequence comprising SEQ ID NO:28.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:30: (AEAKYAKEKLDAYPVIEDLPNLTLEQVMAFIVALENDPSQSSELLSEAKKLNDSQAPK).

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:41: (AEAKYNKEKLDAYPVIEDLPNLTLEQVMAFIVALENDPSQSSELLSEAKKLNDSQAPK).

In certain embodiments, the anti-DR5 polypeptide comprises an amino acid sequence that has at least 90% (e.g., 91%, 92%, 93%, 94%, 95%, 96%, 97%, 98%, 99% or 100%) sequence identity to SEQ ID NO:30 or 41.

In certain embodiments, the anti-DR5 polypeptide comprises an amino acid sequence that has at least 95% (e.g., 96%, 97%, 98%, 99% or 100%) sequence identity to SEQ ID NO:30 or 41.

In certain embodiments, the anti-DR5 polypeptide comprises SEQ ID NO:30 or 41.

In certain embodiments, the anti-DR5 polypeptide consists of SEQ ID NO:30 or 41, which is from N-terminal to C-terminal.

In certain embodiments, the anti-DR5 polypeptide is encoded by a nucleic acid sequence that comprises a sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:36.

DR5 Binder $ABY_{DR5-1}$

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:1 (EQGYAGREIRL), or a sequence having up to 1 or 2 substitutions relative to SEQ ID NO:1.

In certain embodiments, the anti-DR5 polypeptide comprises a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:1 (EQGYAGREIRL).

In certain embodiments, the anti-DR5 polypeptide comprises a helix 1 sequence comprising an amino acid sequence having at least 90% (e.g., 91%, 92%, 93%, 94%, 95%, 96%, 97%, 98%, 99% or 100%) sequence identity to SEQ ID NO:1.

In certain embodiments, the anti-DR5 polypeptide comprises a helix 1 sequence comprising an amino acid sequence having up to 2 substitutions relative to SEQ ID NO: 1. In certain embodiments, the anti-DR5 polypeptide comprises a helix 1 sequence comprising an amino acid sequence having up to 1 substitution relative to SEQ ID NO: 1.

In certain embodiments, the anti-DR5 polypeptide comprises a helix 1 sequence comprising SEQ ID NO:1.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:7 (PQGGAFIGALAD), or a sequence having up to 1 or 2 substitutions relative to SEQ ID NO:7.

In certain embodiments, the anti-DR5 polypeptide comprises a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:7 (PQGGAFIGALAD).

In certain embodiments, the anti-DR5 polypeptide comprises a helix 2 sequence comprising an amino acid sequence having at least 90% (e.g., 91%, 92%, 93%, 94%, 95%, 96%, 97%, 98%, 99% or 100%) sequence identity to SEQ ID NO:7.

In certain embodiments, the anti-DR5 polypeptide comprises a helix 2 sequence comprising an amino acid sequence having up to 2 substitutions relative to SEQ ID NO:7. In certain embodiments, the anti-DR5 polypeptide comprises a helix 2 sequence comprising an amino acid sequence having up to 1 substitution relative to SEQ ID NO:7.

In certain embodiments, the anti-DR5 polypeptide comprises a helix 2 sequence comprising SEQ ID NO:7.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:1, or a sequence having up to 1 or 2 substitutions relative to SEQ ID NO:1; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:7, or a sequence having up to 1 or 2 substitutions relative to SEQ ID NO:7.

In certain embodiments, the anti-DR5 polypeptide comprises:

(a) a helix 1 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:1; and (b) a helix 2 sequence comprising an amino acid sequence having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) sequence identity to SEQ ID NO:7.

In certain embodiments, the anti-DR5 polypeptide comprises:

(a) a helix 1 sequence comprising an amino acid sequence having at least 90% (e.g., 91%, 92%, 93%, 94%, 95%, 96%, 97%, 98%, 99% or 100%) sequence identity to SEQ ID NO:1; and (b) a helix 2 sequence comprising an amino acid sequence having at least 90% (e.g., 91%, 92%, 93%, 94%, 95%, 96%, 97%, 98%, 99% or 100%) sequence identity to SEQ ID NO:7.

In certain embodiments, the anti-DR5 polypeptide comprises a helix 1 sequence comprising an amino acid sequence having up to 2 substitutions relative to SEQ ID NO: 1; and a helix 2 sequence comprising an amino acid sequence having up to 2 substitutions relative to SEQ ID NO:7. In certain embodiments, the anti-DR5 polypeptide comprises a helix 1 sequence comprising an amino acid sequence having up to 1 substitution relative to SEQ ID NO:1; and a helix 2 sequence comprising an amino acid sequence having up to 1 substitution relative to SEQ ID NO:7.

In certain embodiments, the anti-DR5 polypeptide comprises:

(a) a helix 1 sequence comprising SEQ ID NO: 1; and (b) a helix 2 sequence comprising SEQ ID NO: 7.

In certain embodiments, the anti-DR5 polypeptide comprises:

(a) a helix 1 sequence consisting of SEQ ID NO:1; and (b) a helix 2 sequence consisting of SEQ ID NO: 7.

In certain embodiments, the anti-DR5 polypeptide comprises a helix 1 sequence comprising SEQ ID NO:1, a loop 1 sequence comprising SEQ ID NO:18, and a helix 2 sequence comprising SEQ ID NO:7.

In certain embodiments, the anti-DR5 polypeptide comprises a helix 1 sequence comprising SEQ ID NO:1, a loop 1 sequence comprising SEQ ID NO: 18, a helix 2 sequence comprising SEQ ID NO:7, a loop 2 sequence comprising SEQ ID NO:27 and a helix 3 sequence comprising SEQ ID NO:13.

In certain embodiments, the anti-DR5 polypeptide comprises a N-terminal sequence comprising SEQ ID NO:15, a helix 1 sequence comprising SEQ ID NO:1, a loop 1 sequence comprising SEQ ID NO:18, a helix 2 sequence comprising SEQ ID NO:7, a loop 2 sequence comprising SEQ ID NO:27, a helix 3 sequence comprising SEQ ID NO:13 and a C-terminal sequence comprising SEQ ID NO:28.

In certain embodiments, the anti-DR5 polypeptide comprises an amino acid sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:29: (AEAKYAKEQGYAGREIRLLPNLTRPQGGAFIGALADDPSQSSELLSEAKIKLNDSQAPK).

In certain embodiments, the anti-DR5 polypeptide comprises an amino acid sequence that has at least 90% (e.g., 91%, 92%, 93%, 94%, 95%, 96%, 97%, 98%, 99% or 100%) sequence identity to SEQ ID NO:29.

In certain embodiments, the anti-DR5 polypeptide comprises an amino acid sequence that has at least 95% (e.g., 96%, 97%, 98%, 99% or 100%) sequence identity to SEQ ID NO:29.

In certain embodiments, the anti-DR5 polypeptide comprises SEQ ID NO:29.

In certain embodiments, the anti-DR5 polypeptide consists of SEQ ID NO:29, which is from N-terminal to C-terminal.

Certain embodiments of the invention also provide an isolated nucleic acid encoding an isolated polypeptide as described herein.

Certain embodiments of the invention provide an expression cassette comprising a nucleic acid as described herein and a promoter.

Certain embodiments provide a vector comprising a nucleic acid or an expression cassette described herein.

Certain embodiments provide a cell comprising a vector or a nucleic acid, or an expression cassette as described herein. In certain embodiments, the cell is a mammalian cell or a bacterial cell (e.g., *E. coli*).

In certain embodiments, the anti-DR5 polypeptide is encoded by a nucleic acid sequence that comprises a sequence that has at least 85% (e.g., 86%, 87%, 88%, 89%, 90%, 91%, 92%, 93%, 94%, 95%, 96%, 97%, 98%, 99% or 100%) sequence identity to SEQ ID NO:35.

METHODS OF USE

Certain embodiments of the invention provide methods of inhibiting the activity of DR5 in a cell, comprising contacting DR5 with an isolated polypeptide described herein. In certain embodiments, DR5 is contacted in vitro. In certain embodiments, DR5 is contacted in vivo. In certain embodiments, the activity of DR5 is inhibited by at least about 25% (e.g., 25%, 30%, 35%, 40%, 45%, 50%, 55%, 60%, 65%, 70%, 80%, 90% or more) as compared to a control. In certain embodiments, the activity of DR5 is inhibited by at least about 45% (e.g., 50%, 55%, 60%, 65%, 70%, 80%, 90% or more) as compared to a control (e.g., in the absence of the polypeptide).

In certain embodiments, the activity of DR5 is inhibited by a polypeptide described herein via promoting a DR5 conformational change into an inactive conformation.

In certain embodiments, TRAIL-induced recruitment of Fas-associated death domain (FADD) is inhibited by at least about 25% (e.g., 25%, 30%, 35%, 40%, 45%, 50%, 55%, 60%, 65%, 70%, 80%, 90% or more) in the presence of an anti-DR5 polypeptide described herein, as compared to a control.

In certain embodiments, the TRAIL-induced activation of caspase-8 is inhibited by at least about 25% (e.g., 25%, 30%, 35%, 40%, 45%, 50%, 55%, 60%, 65%, 70%, 80%, 90% or more) in the presence of an anti-DR5 polypeptide described herein, as compared to a control.

In certain embodiments, the TRAIL-induced apoptosis is inhibited by at least about 25% (e.g., 25%, 30%, 35%, 40%, 45%, 50%, 55%, 60%, 65%, 70%, 80%, 90% or more) in the presence of an anti-DR5 polypeptide described herein, as compared to a control.

In certain embodiments, the DR5-mediated apoptosis is inhibited by at least about 25% (e.g., 25%, 30%, 35%, 40%, 45%, 50%, 55%, 60%, 65%, 70%, 80%, 90% or more) in the presence of an anti-DR5 polypeptide described herein, as compared to a control.

In certain embodiments, TRAIL-induced hepatocyte cytotoxicity is inhibited by at least about 25% (e.g., 25%, 30%, 35%, 40%, 45%, 50%, 55%, 60%, 65%, 70%, 80%, 90% or more) in the presence of an anti-DR5 polypeptide described herein, as compared to a control.

In certain embodiments, fatty acid-induced hepatocyte cytotoxicity (e.g., hepatocyte lipoapoptosis) is inhibited by at least about 25% (e.g., 25%, 30%, 35%, 40%, 45%, 50%, 55%, 60%, 65%, 70%, 80%, 90% or more) in the presence of an anti-DR5 polypeptide described herein, as compared to a control.

In certain embodiments, DR5-mediated hepatocyte cytotoxicity is inhibited by at least about 25% (e.g., 25%, 30%, 35%, 40%, 45%, 50%, 55%, 60%, 65%, 70%, 80%, 90% or more) in the presence of an anti-DR5 polypeptide described herein, as compared to a control.

Certain embodiments of the invention provide an isolated polypeptide as described herein for use in diagnosis or medical therapy.

Certain embodiments of the invention provide a method of treating a DR5 related disease or disorder in a mammal, comprising administering an effective amount of an isolated polypeptide as described herein to the mammal.

Certain embodiments of the invention provide an isolated polypeptide as described herein for the prophylactic or therapeutic treatment of a DR5 related disease or disorder.

Certain embodiments of the invention provide the use of an isolated polypeptide as described herein to prepare a medicament for the treatment of a DR5 related disease or disorder in a mammal.

Certain embodiments of the invention provide a method of treating a fatty liver disorder in a mammal, comprising administering an effective amount of an isolated polypeptide as described herein to the mammal.

Certain embodiments of the invention provide an isolated polypeptide as described herein for the prophylactic or therapeutic treatment of a fatty liver disorder.

Certain embodiments of the invention provide the use of an isolated polypeptide as described herein to prepare a medicament for the treatment of a fatty liver disorder in a mammal.

In certain embodiments, the fatty liver disorder is non-alcoholic fatty liver disease (NAFLD), nonalcoholic steatohepatitis (NASH), or cirrhosis. In certain embodiments, the fatty liver disorder is non-alcoholic fatty liver disease (NAFLD).

In certain embodiments, the mammal is human.

Certain embodiments of the invention provide methods of detecting the presence and/or level of DR5 in a cell, comprising contacting the cell with an isolated polypeptide as described herein, and detecting whether a complex is formed between the isolated polypeptide and DR5.

In certain embodiments, the cell is contacted in vitro. In certain embodiments, the cell is contacted in vivo. In certain embodiments, the detecting comprises detecting fluorescent signal, radionuclide signal or immunohistochemical staining signal.

Administration

Certain embodiments of the invention provide a composition comprising the isolated polypeptide having affinity for Death Receptor 5, and a carrier.

For in vivo use, a polypeptide of the invention is generally incorporated into a pharmaceutical composition prior to administration. Within such compositions, one or more polypeptides of the invention may be present as active ingredient(s) (i.e., are present at levels sufficient to provide a statistically significant effect on the symptoms of a relevant disease (e.g., fatty liver condition), as measured using a representative assay). A pharmaceutical composition comprises one or more such polypeptides in combination with any pharmaceutically acceptable carrier(s) known to those skilled in the art to be suitable for the particular mode of administration. In addition, other pharmaceutically active ingredients (including other therapeutic agents) may, but need not, be present within the composition.

In certain embodiments, the present polypeptides (i.e., affibody of the present invention or a fragment thereof) may be systemically administered, e.g., intravenously, subcutaneously, intradermally, orally, in combination with a pharmaceutically acceptable vehicle such as an inert diluent or an assimilable edible carrier. They may be freeze-dried into lyophilized formulation (e.g., lyophilized cake), may be formulated or reconstituted as a liquid dosage form, may be enclosed in hard or soft shell gelatin capsules, may be compressed into tablets, or may be incorporated directly with the food of the patient's diet. For oral therapeutic administration, the polypeptide may be combined with one or more excipients and used in the form of ingestible tablets, buccal tablets, troches, capsules, elixirs, suspensions, syrups, wafers, and the like. Such compositions and preparations should contain at least 0.1% of a polypeptide of the present invention. The percentage of the compositions and preparations may, of course, be varied and may conveniently be between about 2 to about 60% of the weight of a given unit dosage form. The amount of polypeptide in such therapeutically useful compositions is such that an effective dosage level will be obtained.

Lyophilized formulation may also contain bulking agent (e.g., mannitol or glycine) and cryoprotectant/lyoprotectant (e.g., trehalose or sucrose). Lyophilized formulation can be reconstituted into a liquid dosage form using saline, 5% dextrose solution or water before administration. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptide, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptide may be incorporated into sustained-release preparations and devices.

The polypeptide may be administered intravenously, subcutaneously, intradermally or intraperitoneally by infusion or injection. Additionally, the polypeptide may be administered by local injection, such as by subcutaneous injection or intradermal injection. Solutions of the polypeptide may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the polypeptide that are adapted for the extemporaneous preparation of sterile injectable or infusible solutions or dispersions, optionally encapsulated in liposomes or nanoparticles. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polypeptide in the required amount in the appropriate solvent with various of the other ingredients enumerated above, as required, followed by filter sterilization. In the case of sterile powders for the preparation of sterile injectable solutions, the methods of preparation are vacuum drying and the freeze drying techniques, which yield a powder of the polypeptide plus any additional desired ingredient present in the previously sterile-filtered solutions.

For topical administration, the present polypeptide may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present polypeptides can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the polypeptides of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the polypeptides of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of a polypeptide of the present invention required for use in treatment will vary with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Polypeptides of the invention can also be administered in combination with other therapeutic agents and/or treatments, such as other agents or treatments that are useful for the treatment of DR5 related diseases or disorders, such as fatty liver diseases. Non-limiting examples of such agents include vitamin E, obesity drugs or lipase inhibitors (e.g., orlistat) and diabetes treatment (e.g., pioglitazone). Additionally, one or more polypeptides of the invention may be administered (e.g., a combination of polypeptides may be administered). Accordingly, one embodiment the invention also provides a composition comprising a polypeptide of the invention, at least one other therapeutic agent, and a pharmaceutically acceptable diluent or carrier. The invention provides a kit comprising a polypeptide of the invention, packaging material, and instructions for administering a polypeptide of the invention to a mammal to treat fatty liver diseases. The invention also provides a kit comprising a polypeptide of the invention, at least one other therapeutic agent, packaging material, and instructions for administering a polypeptide of the invention and the other therapeutic agent or agents to a mammal to treat fatty liver diseases.

As used herein, the term "therapeutic agent" refers to any agent or material that has a beneficial effect on the mammalian recipient.

Certain Definitions

The term "anti-DR5 polypeptide" or "DR5-specific polypeptide" as used herein refers to an isolated anti-DR5 polypeptide or an isolated polypeptide that binds DR5. For example, the polypeptide has at least a $K_d$ of 10 μM or stronger binding as determined in the binding affinity measurement assay(s) in the Example 1 or in Vunnam, et al., *Biochemistry* 2020 59 (40), 3856-3868, DOI: 10.1021/acs.biochem.0c00529, which is incorporated by reference herein for all purposes.

The term "inhibitor of DR5" as used herein refers to an isolated anti-DR5 polypeptide (e.g., an affibody or fragment thereof) that is capable of inhibiting the function of DR5 (e.g., inhibits signal transduction activity). For example, in certain embodiments, the isolated anti-DR5 polypeptide, detectably inhibits the biological activity of DR5 as measured, e.g., using an assay described herein. In certain embodiments, the isolated anti-DR5 polypeptide, inhibits the biological activity of DR5 by at least about 5%, at least about 10%, at least about 20%, at least about 30%, at least about 40%, at least about 50%, at least about 60%, at least about 70%, at least about 80%, or at least about 90%. In certain embodiments, isolated anti-DR5 polypeptide is a selective inhibitor of DR5. For example, an affibody of the invention may be at least 5, at least 10, at least 50, at least 100, at least 500, or at least 1,000 fold selective for DR5 over another TNFR (e.g., DR4 or TNFR1) in a selected assay (e.g., an assay described in the Example 1 herein).

In certain embodiments, one or more amino acid residues are mutated within the polypeptide as described herein. For example, the mutation is conducted via error-prone PCR or site directed mutagenesis. In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each helix, and specifically within 35%, and still more specifically within 30% (e.g., within 25%). The identity of amino acid sequences can be determined as described herein. In certain embodiments, one or more amino acid residue is mutated into one that is a non-conservative substitution.

In certain embodiments, the development of the polypeptides having affinity for DR5 involve a display technology (e.g., yeast surface display, phage display, bacterial display, mRNA display or ribosomal display).

The polypeptides obtained can be purified to homogeneity. The polypeptides can be isolated and purified by a method routinely used to isolate and purify proteins. The polypeptides can be isolated and purified by the combined use of one or more methods appropriately selected from column chromatography, filtration, ultrafiltration, salting out, dialysis, preparative polyacrylamide gel electrophoresis, and isoelectro-focusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography (e.g., metal affinity chromatography), ion exchange chromatography, hydrophobic chromatography, gel filtration, reverse-phase chromatography, and adsorption chromatography. These chromatographic methods can be practiced using liquid phase chromatography, such as HPLC and FPLC. The polypeptides can also be purified by utilizing target binding, using carriers on which targets have been immobilized.

The polypeptides of the present invention can be formulated according to standard methods (see, for example, Remington's Pharmaceutical Science, latest edition, Mark Publishing Company, Easton, U.S.A.), and may comprise pharmaceutically acceptable carriers and/or additives. The present invention relates to compositions (including reagents and pharmaceuticals) comprising the polypeptides of the invention, and pharmaceutically acceptable carriers and/or additives. Other exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

The terms "polypeptide" and "protein" are used interchangeably herein. A protein molecule may exist in an isolated or purified form or may exist in a non-library environment such as, for example, an isolated or purified form as an active ingredient of a drug dosage form or a diagnostic reagent. Fragments and variants of the disclosed proteins or partial-length proteins encoded thereby are also encompassed by the present invention. By "fragment" or "portion" is meant a full length or less than full length of the amino acid sequence of a protein.

The invention encompasses isolated or substantially purified protein compositions. In the context of the present invention, an "isolated" or "purified" polypeptide is a polypeptide that exists apart from its native or library environment. A polypeptide may exist in a purified form or may exist in a non-native environment such as, for example, a transgenic host cell such as a bacterium or a mammalian expression system for the production of the polypeptide. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "comparison window" makes reference to a contiguous and specified segment of an amino acid or polynucleotide sequence, wherein the sequence in the comparison window may comprise additions or deletions (i.e., gaps) compared to the reference sequence (which does not comprise additions or deletions) for optimal alignment of the two sequences. Generally, the comparison window is at least about 20 contiguous amino acid residues or nucleotides in length, and optionally can be 30, 40, 50, 100, or longer.

As used herein, "percentage of sequence identity" means the value determined by comparing two optimally aligned sequences over a comparison window, wherein the portion of the polypeptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least about 70%, 71%, 72%, 73%, 74%, 75%, 76%, 77%, 78%, or 79%, at least about 80%, 81%, 82%, 83%, 84%, 85%, 86%, 87%, 88%, or 89%, at least about 90%, 91%, 92%, 93%, or 94%, and at least about 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least about 70%, at least about 80%, 90%, or at least about 95%.

The term "substantial identity" in the context of a peptide indicates that a peptide comprises a sequence with at least about 70%, 71%, 72%, 73%, 74%, 75%, 76%, 77%, 78%, or 79%, 80%, 81%, 82%, 83%, 84%, 85%, 86%, 87%, 88%, or 89%, at least about 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity or complementarity for the test sequence(s) relative to the reference sequence, based on the designated program parameters.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., dehydroalanine, homoserine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a (C1-C6)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein) The term also comprises natural and unnatural amino acids bearing a cyclopropyl side chain or an ethyl side chain.

The term "nucleic acid" and "polynucleotide" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

A "vector" is defined to include, inter alia, any plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Operably-linked" may refer to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

The term "therapeutically effective amount," in reference to treating a disease state/condition, refers to an amount of a polypeptide either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder, such as fatty liver disease. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The invention will now be illustrated by the following non-limiting Example.

Example 1. Noncompetitive Allosteric Antagonism of Death Receptor 5 by an Affibody Discovered Via Yeast Display Tumor necrosis factor (TNF) ligands and TNF receptors (TNFR) are essential modulators of the immune response and are critically involved in organ development and tissue homeostasis (Chan, et al., Immunity, 2000. 13(4): p. 419-22). Activation of the TNFR members via their cognate ligands effects cell proliferation, survival, and apoptosis. Excessive or impaired cell death is associated with pathophysiology of several acute and chronic diseases, including developmental, autoimmune, neurodegenerative diseases, and cancer (Apostolaki, M., et al., Curr Dir Autoimmun, 2010. 11: p. 1-26; Matsuno, H., et al., Rheumatology (Oxford), 2002. 41(3): p. 329-37). Neutralization of TNF-α with monoclonal antibodies has significant clinical benefit in patients with rheumatoid arthritis, inflammatory bowel disease, and psoriasis (Matsuno, H., et al., Rheumatology (Oxford), 2002. 41(3): p. 329-37; Lin, J., et al., Clin Immunol, 2008. 126(1): p. 13-30). Moreover, several agonistic death receptor-specific antibodies are in various stages of clinical trials (Wiezorek, J., P. Holland, and J. Graves, Clin Cancer Res, 2010. 16(6): p. 1701-8). However, the global blockade of TNF ligand causes several undesirable side effects, such as tuberculosis, pneumonia, and an increased risk of lymphomas (Wolfe, F. and K. Michaud, Arthritis Rheum, 2004. 50(6): p. 1740-51; and Kang, M. J., et al., Korean J Intern Med, 2007. 22(1): p. 63-6). Recent breakthroughs regarding the structure and biophysics of TNF receptors have shifted the current therapeutic paradigm of global TNF ligand inhibition to selective targeting of the receptor itself (Fricke, F., et al., Histochemistry and Cell Biology, 2014. 142(1): p. 91-101; Valley, C. C., et al., J Biol Chem, 2012. 287(25): p. 21265-78). In particular, blocking oligomerization of TNF receptors has been considered a potential therapeutic target (Chan, F. K., Annals of the Rheumatic Diseases, 2000. 59(Suppl 1): p. i50-i53; Deng, G.-M., et al., Nat Med, 2005. 11(10): p. 1066-1072). In our previous work, we showed that it is possible to inhibit TNFR signaling by specifically targeting the receptor dimer, without interrupting ligand binding (Lo, C. H., et al., SLAS Discov, 2017: p. 2472555217706478; Vunnam, N., et al., J Mol Biol, 2017. 429(19): p. 2943-2953). However, despite progress, these approaches and others like them have failed to discover even nanomolar potency small molecule inhibitors. These studies have been limited to molecules that competitively target the receptor-receptor or receptor-ligand interfaces. Non-competitive agents have the potential for greater efficacy. Also, protein ligands may provide larger surface area for elevated affinity (Chen, J., N. Sawyer, and L. Regan, Protein Sci, 2013. 22(4): p. 510-5) and target a wider array of epitopes.

Recently, non-antibody protein scaffolds with picomolar affinities have been discovered from affibody libraries to numerous targets, including tumor necrosis factor α, human epidermal growth factor receptor 2, and amyloid-O peptide (Stahl, S., et al., Trends Biotechnol, 2017. 35(8): p. 691-712). Affibody molecules are small ligands based on the three helical bundle Z domain of the Ig-binding region of protein A (Nygren, P. A., FEBS J, 2008. 275(11): p. 2668-76; Nord, K., et al., Nat Biotechnol, 1997. 15(8): p. 772-7). Combinatorial libraries containing different affibody molecules have been generated by diversifying 17 solvent-exposed amino acids located in helices 1 and 2 of the Z domain (Stahl, S., et al., Trends Biotechnol, 2017. 35(8): p. 691-712; Woldring, D. R., et al., Biochemistry, 2017. 56(11): p. 1656-1671). The small size, robust structure, high affinity binding ability to protein targets, efficient conjugation, and relatively easy production procedures—either by chemical synthesis or by recombinant production in bacteria—makes them attractive targeting agents for therapeutics and diagnostics (Stahl, S., et al., Trends Biotechnol, 2017. 35(8): p. 691-712).

In the current study, we used an affibody library composed of $2\times10^9$ variants along with directed evolution to discover a high affinity functional modulator of death receptor 5 (DR5; also known as TRAIL-R2 or APO-2), a member of TNF receptor superfamily. Upon binding to its cognate ligand, tumor necrosis factor-related apoptosis-inducing ligand (TRAIL), DR5 recruits the adaptor molecule Fas-associated death domain (FADD), activating caspase-8, subsequently leading to apoptosis (Ashkenazi, A. and V. M. Dixit, Science, 1998. 281(5381): p. 1305-8; Kischkel, F. C., et al., Immunity, 2000. 12(6): p. 611-20). Recent studies show that liver expression of DR5 is increased in both human and experimental nonalcoholic steatohepatitis (NASH) (Hirsova, P. and G. J. Gores, Cell Mol Gastroenterol Hepatol, 2015. 1(1): p. 17-27). Hepatocyte apoptosis by free fatty acids is considered to be a key histological feature of NASH and plays a critical role in pathogenesis of non-alcoholic fatty liver disease (NAFLD) (Cazanave, S. C. and G. J. Gores, Clin Lipidol, 2010. 5(1): p. 71-85; Hirsova, P., et al., J Lipid Res, 2016. 57(10): p. 1758-1770). In vitro studies of NAFLD showed that hepatocyte treatment with free fatty acid palmitate leads to DR5 clustering in the plasma membrane, which triggers ligand-independent receptor activation and hepatocyte cytotoxicity (Cazanave, S. C., et al., J Biol Chem, 2011. 286(45): p. 39336-48). In hepatocellular carcinoma cells (Huh-7), knockdown of DR5 expression attenuates fatty acid mediated apoptosis (Cazanave, S. C., et al., J Biol Chem, 2011. 286(45): p. 39336-48). Likewise, in a dietary mouse model of NASH, DR5 deletion suppresses hepatocyte apoptosis and fibrosis (Idrissova, L., et al., J Hepatol, 2015. 62(5): p. 1156-63). Furthermore, inhibitors of apoptosis have been developed as drugs for the treatment of NASH (Anstee, Q. M., et al., J Hepatol, 2010. 53(3): p. 542-50). Therefore, inhibition of TRAIL-induced and/or fatty acid-induced activation of DR5 signaling is an attractive strategy for NASH therapy.

Utilizing yeast surface display (Chao, G., et al., Nat Protoc, 2006. 1(2): p. 755-68) and directed evolution, we identified an affibody variant that specifically binds to human DR5 with high affinity. Cell-based functional assays showed that the affibody inhibits TRAIL- and palmitate-induced apoptosis in Huh-7 cells, an in vitro model for NAFLD and NASH. Using a combination of biophysical and biochemical studies, we showed that the affibody does not block TRAIL binding or disrupt DR5-DR5 interactions. These results suggest that the affibody allosterically inhibits DR5 signaling. In summary, we have discovered a non-immunoglobulin and non-competitive DR5 antagonist that can serve as a potential drug candidate for NASH.

Results and Discussion

Figure 2A:
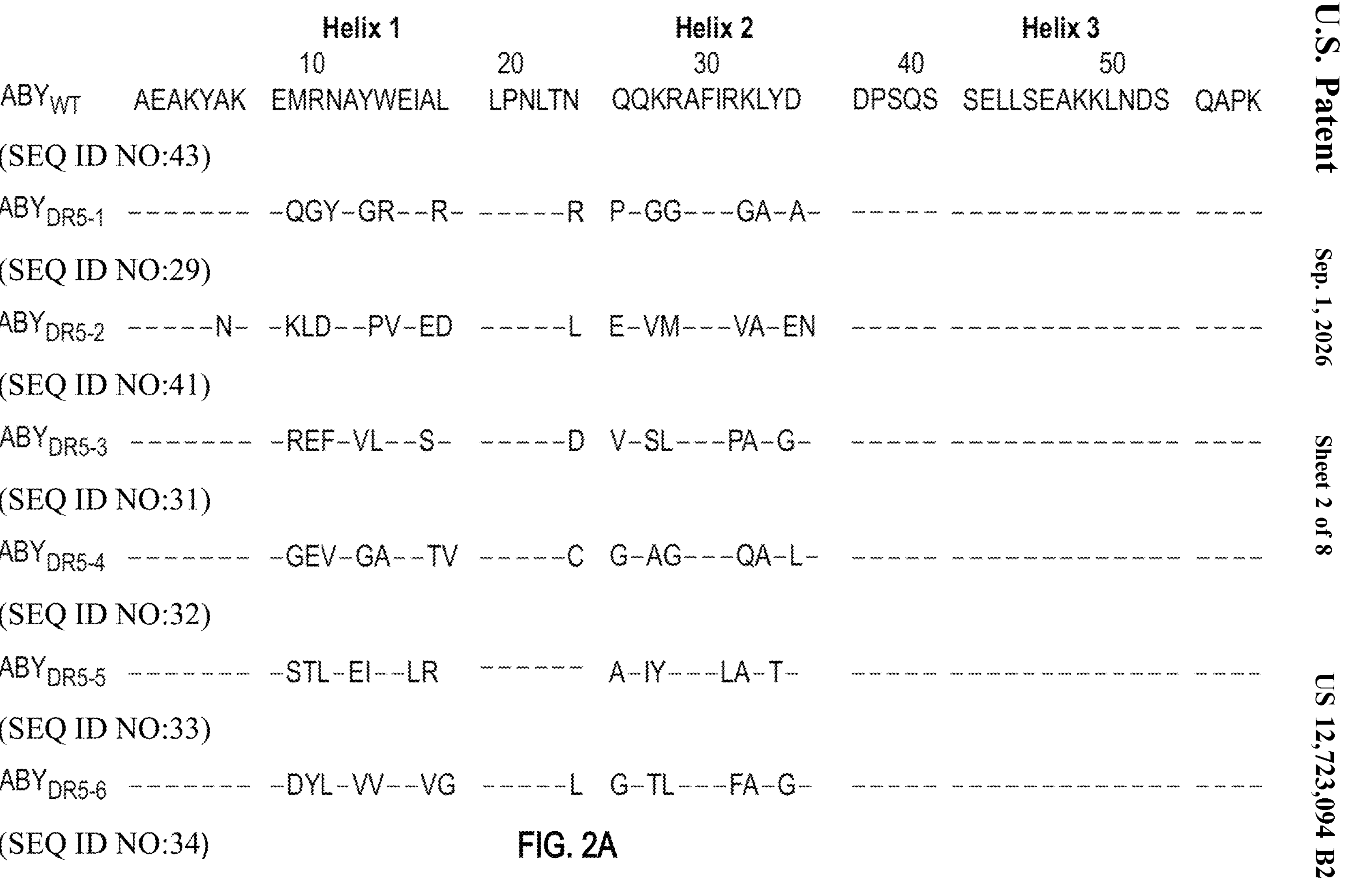
FIGS. 2A-2D. Binding affinity measurements of ABY variants to DR5ΔCD-GFP on HEK293 cells.
Figures 2B, 2C, 2D:
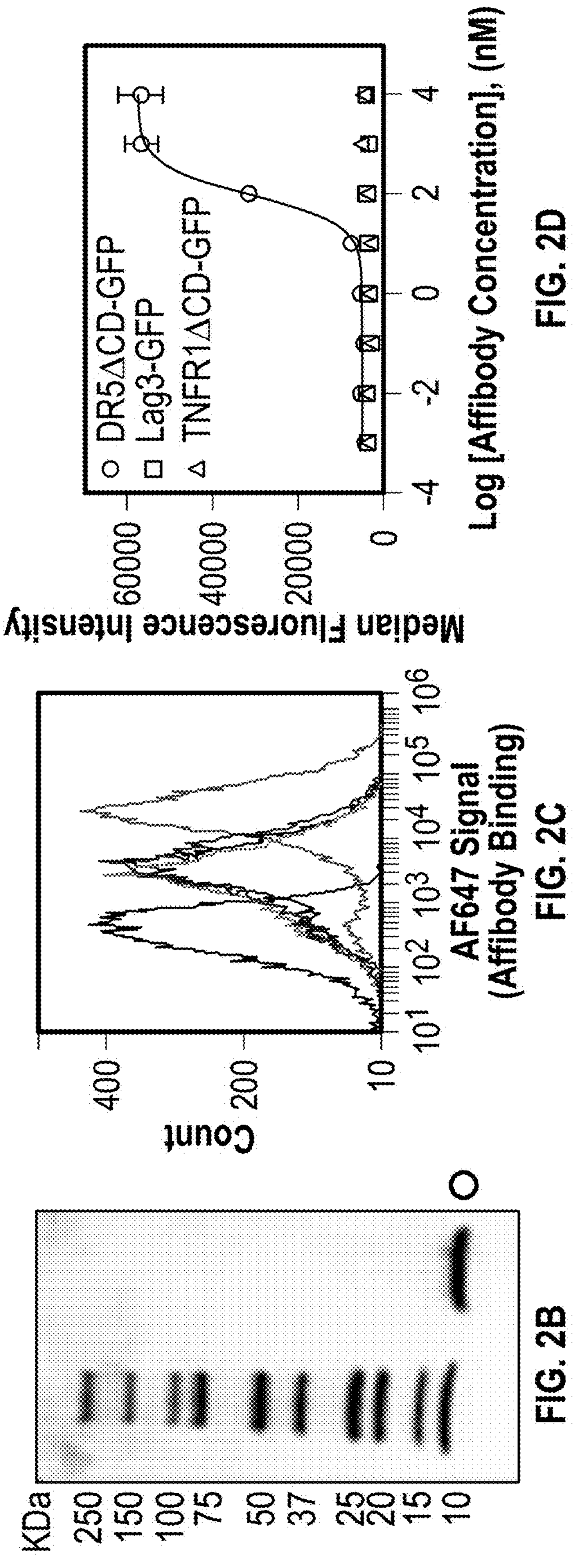

Identification and Evolution of DR5-Specific ABY Binders Using Yeast Surface Display Yeast surface display, with magnetic and flow cytometric selection methods, was used to isolate affibody molecules with specific binding to the extracellular domain of DR5. The previously described (Woldring, D. R., et al., Biochemistry, 2017. 56(11): p. 1656-1671) naïve yeast surface display affibody library comprises $2\times10^9$ unique affibody variants with designed diversity at 17 sites on the surface of two helices (FIG. 1A). To enrich specific binders with a high likelihood to bind DR5 in its cellular conformation (Stem, L. A., et al., ACS Comb Sci, 2019. 21(3): p. 207-222) the DR5 molecular target was isolated from the lysate of mammalian cells expressing long isoform of DR5 with a deleted cytoplasmic domain replaced by green fluorescent protein (DR5ΔCD-GFP). The GFP enables purified immobilization on magnetic beads via anti-GFP antibody and fluorescent detection via FACS. An analogous construct with lymphocyte-activation gene 3 (LAG3)-GFP served as a negative control (FIG. 1B). LAG3 is an immune checkpoint receptor protein found on the cell surface of effector T cells that has a very low sequence homology (15%) with DR5. During each evolutionary round, the ABY library underwent three magnetic sorts to enrich DR5-specific binders and one FACS sort for the presence of the C-terminal peptide epitope to isolate full-length affibodies. Sorted DR5-binding ABY sequences were mutated through error-prone PCR targeting the helical paratope and the genes of enriched ABY variants (Hackel, B. J., A. Kapila, and K. D. Wittrup, J Mol Biol, 2008. 381(5): p. 1238-52). The mutagenized ABY population was further enriched with two magnetic sorts with DR5ΔCD-GFP coated beads and one FACS with DR5ΔCD-GFP expressing cell lysates. After these six rounds of sorting and one round of mutagenesis, the enriched population exhibited substantial binding to DR5ΔCD-GFP (FIG. 1C) whereas significant binding was not observed to LAG3-GFP cell lysate (FIG. 1D), which suggests that the populations evolved specifically with DR5-ABY interactions rather than non-specific interactions in the selection process. From this evolved population, we sequenced six randomly selected clones, which revealed high sequence diversity in the functional population with amino acid variations at the initially diversified helical sites (FIG. 2A). The six DR5 binders were produced in *E. coli* and purified by metal affinity chromatography. Electrophoresis revealed good yields (~1 mg/L), high purity, and proper molecular weight of all soluble proteins (FIG. 2B).

Binding Affinity Measurements of ABY Variants to DR5A CD-GFP on HEK293 Cells

Figures 6A, 6B, 7A, 7B, 7C:
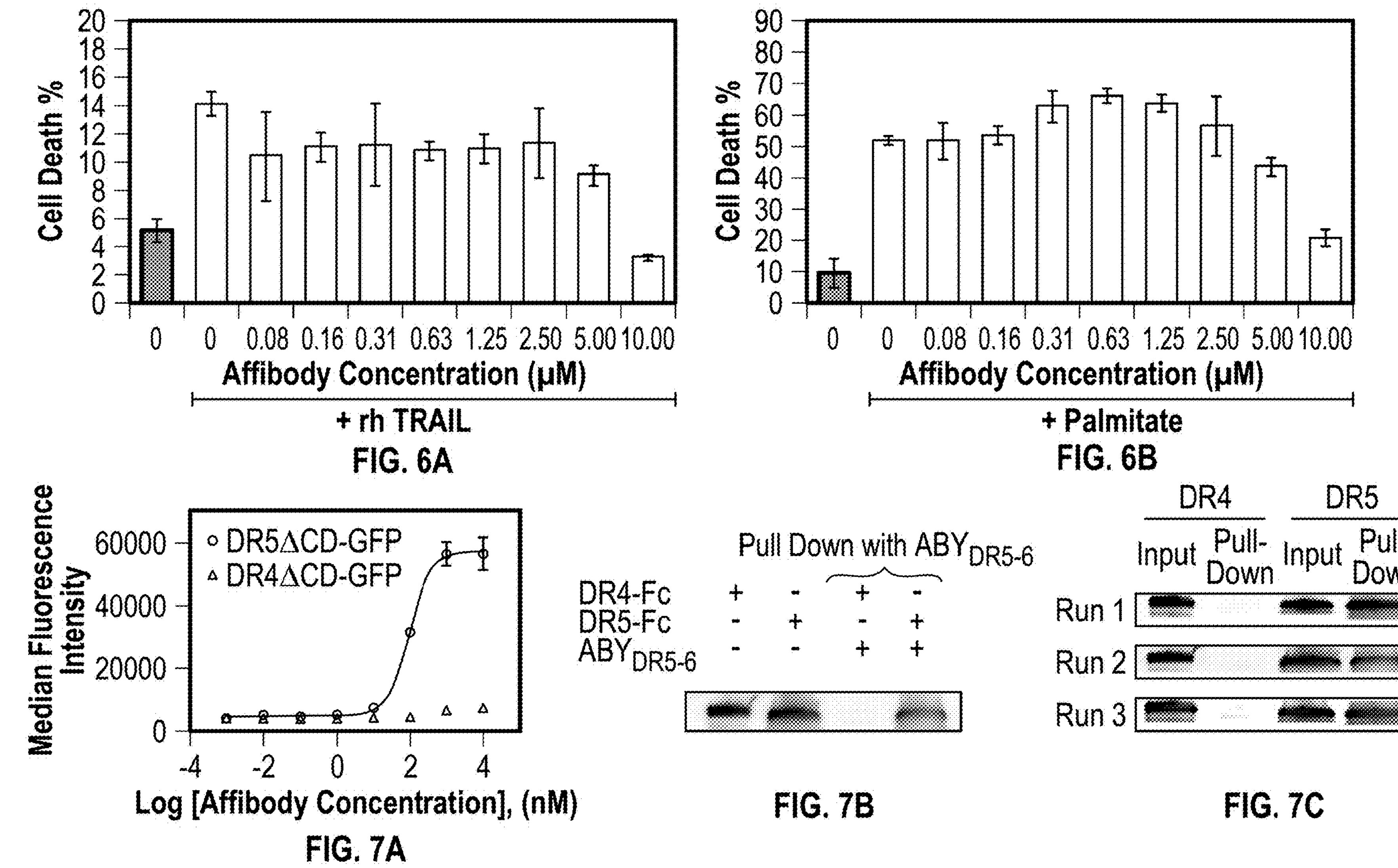
FIGS. 6A-6B. Effect of $ABY_{DR5-6}$ on lipoapoptosis in Huh-7 hepatocytes.
FIGS. 7A-7C. Binding of ABY variants to DR4.

To test the binding of soluble ABY variants to DR5, HEK293 cells with stable expression of DR5ΔCD-GFP were incubated, separately, with each of the six soluble ABY variants ($ABY_{DR5}$). Among these six variants, five clones showed weak binding and one clone ($ABY_{DR5-6}$) showed significant binding to DR5ΔCD-GFP cells (FIG. 2C). Subsequently, we measured the binding affinity of $ABY_{DR5-6}$ to DR5 in HEK293 cells with stable expression of DR5ΔCD-GFP. Titration exhibited an affinity of $K_d$=94±5 nM to DR5ΔCD-GFP, while no significant binding was observed to cells expressing TNFR1ΔCD-GFP or LAG3-GFP (FIG. 2D). To further verify $ABY_{DR5-6}$ Specificity, we tested binding to death receptor 4 (DR4), which is a homologous member (51% identity and 68% similarity to DR5) of the TNF-receptor superfamily that binds to TRAIL and triggers apoptosis (Pan, G., et al., Science, 1997. 277(5327): p. 815-8; Pan, G., et al., Science, 1997. 276(5309): p. 111-3). No significant binding was observed to cells expressing DR4ΔCD-GFP (FIG. 7A). To further support this observation, a pull-down assay was performed, in which $ABY_{DR5-6}$ was immobilized on anti-His6 beads and incubated with DR5 and DR4, to assess $ABY_{DR5-6}$ binding to DR5 and DR4. Western blot analysis of pull-down samples showed that $ABY_{DR5-6}$ does not bind to DR4; only DR5 appeared in the pulled-down samples (FIGS. 7B-7C). These results confirm that the ABY variant specifically binds DR5 rather than non-specifically binding other proteins expressed on the surface of HEK293 cells.

Colocalization of Membrane Bound DR5A CD-GFP and $ABY_{DR5-6}$

Figure 8:
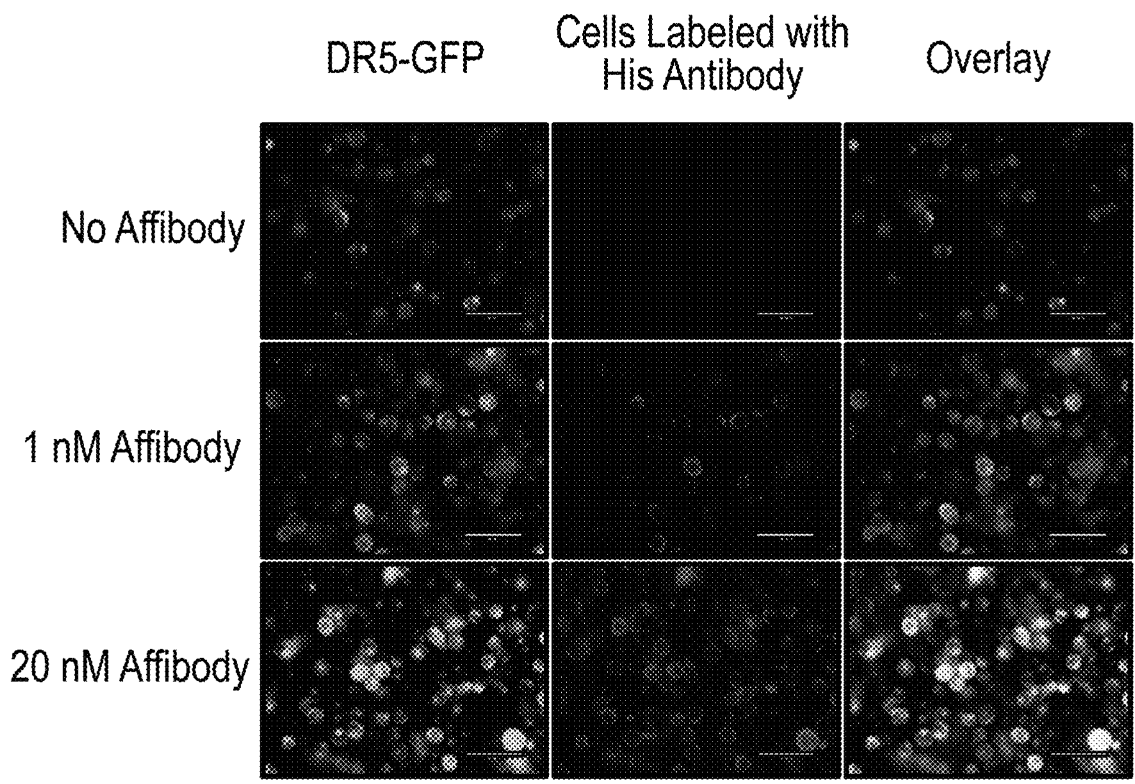
FIG. 8. Colocalization of membrane-bound DR5ΔCD-GFP and $ABY_{DR5-6}$ on HEK293 cell surface. The overlay of the His staining and GFP signals indicates colocalization of $ABY_{DR5-6}$ and DR5ΔCD-GFP. Scale bars correspond to 100 μm.

Next, we sought to directly observe the binding of the $ABY_{DR5-6}$ molecule to DR5ΔCD-GFP expressed on the cell surface. For this assay, we incubated DR5ΔCD-GFP stably expressing cells with $ABY_{DR5-6}$ binder and observed colocalization with fluorescence microscopy (FIG. 8). However, some cells were only stained with AlexaFluor-labeled affibody, which might be originating from binding of $ABY_{DR5-6}$ to endogenous DR5 (very low levels) in HEK293 cells. These results confirm the direct interaction between affibody and DR5. Next, we sought to study the effect of $ABY_{DR5-6}$ binder on biological function of DR5.

Effect of $ABY_{DR5-6}$ on TRAIL-Induced Apoptosis

It is well documented that TRAIL selectively induces apoptosis in several different cancer cells without harming normal cells, and DR5 is implicated as the primary TRAIL target (Ashkenazi, A. and V. M. Dixit, Science, 1998. 281(5381): p. 1305-8; Walczak, H., et al., Nat Med, 1999. 5(2): p. 157-63). To test the biological effect of ABY binding to DR5 on TRAIL-induced apoptosis, functional assays were performed with the human lymphoma Jurkat cell line, which is a well-established model for the study of the apoptotic death pathways (Gottlieb, R. A., et al., Proc Natl Acad Sci USA, 1996. 93(2): p. 654-8). We first examined the surface expression of DR5 in Jurkat cells using flow cytometry, which showed significant expression of DR5 (FIG. 3A). Next, the functional effect of $ABY_{DR5-6}$ on TRAIL-induced apoptosis was determined by MTT assay. $ABY_{DR5-6}$ inhibited TRAIL-induced apoptosis in a dose-dependent manner ($IC_{50}$ of 15±1 nM), while nonbinding ABYNB control caused no effect (FIG. 3B).

To further understand the effect of $ABY_{DR5-6}$ on downstream signaling of the DR5 apoptotic pathway, we examined the TRAIL-induced recruitment of FADD to DR5 and activation of caspase-8 (Kischkel, F. C., et al., Immunity, 2000. 12(6): p. 611-20) in the presence or absence of $ABY_{DR5-6}$. Co-immunoprecipitation showed that cells treated with $ABY_{DR5-6}$ significantly inhibited TRAIL-induced recruitment of FADD to DR5 compared with untreated cells (FIG. 3C). Subsequently, we examined the activation of caspase-8, a further downstream cell death signaling protein, in response to affibody treatment. $ABY_{DR5-6}$ inhibited TRAIL-induced caspase-8 activation in a dose-dependent manner, with an $IC_{50}$ of 160±20 nM (FIG. 3D). Taken together, these results confirm that soluble $ABY_{DR5-6}$ is a functional inhibitor of TRAIL-induced apoptosis.

Effect of $ABY_{DR5-6}$ on TRAIL-DR5 Interactions

Figure 4A:
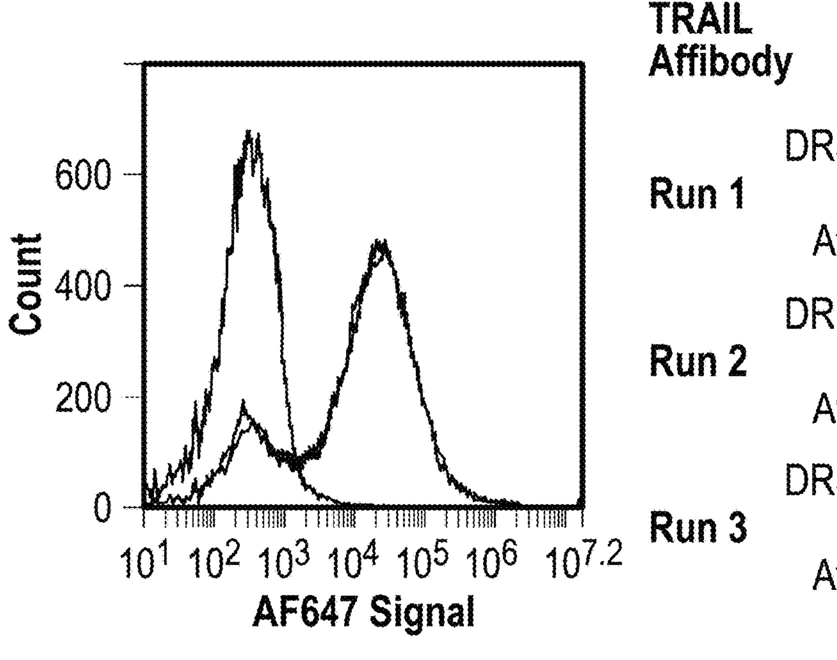
FIGS. 4A-4B. $ABY_{DR5-6}$ binds DR5 without competing TRAIL-DR5 complex formation.
Figure 4B:
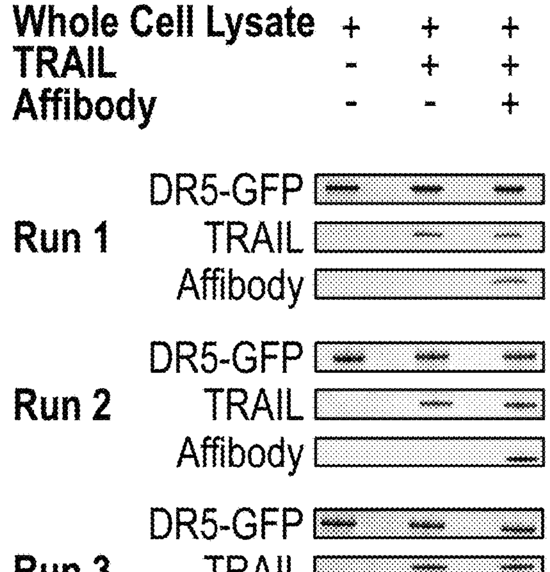

It has been shown previously that blocking TRAIL binding to DR5 inhibits apoptosis (Valley, C. C., et al., J Biol Chem, 2012. 287(25): p. 21265-78; Clancy, L., et al., Proc Natl Acad Sci USA, 2005. 102(50): p. 18099-104). We therefore investigated if the inhibitory function of $ABY_{DR5-6}$ on TRAIL-induced apoptosis resulted from blocking TRAIL binding. We tested the effect of $ABY_{DR5-6}$ on TRAIL-DR5 interactions in live cells using flow cytometry (FIG. 4A). No significant difference was observed in TRAIL binding to DR5ΔCD-GFP expressing cells in the presence versus absence of $ABY_{DR5-6}$. To further support this observation, a pull-down assay was used to assess the effect of $ABY_{DR5-6}$ on TRAIL-DR5 interactions. Western blot analysis of pull-down samples showed that $ABY_{DR5-6}$ does not affect TRAIL binding: DR5 and TRAIL interacted similarly in the presence or absence of $ABY_{DR5-6}$ (FIG. 4B). Moreover, $ABY_{DR5-6}$ also appeared in the pulled-down sample, which suggests that TRAIL and $ABY_{DR5-6}$ are binding at different sites in DR5. These results confirm that DR5 binder does not block TRAIL binding.

Effect of $ABY_{DR5-6}$ on Ligand-Independent DR5-DR5 Interactions

Figure 5:
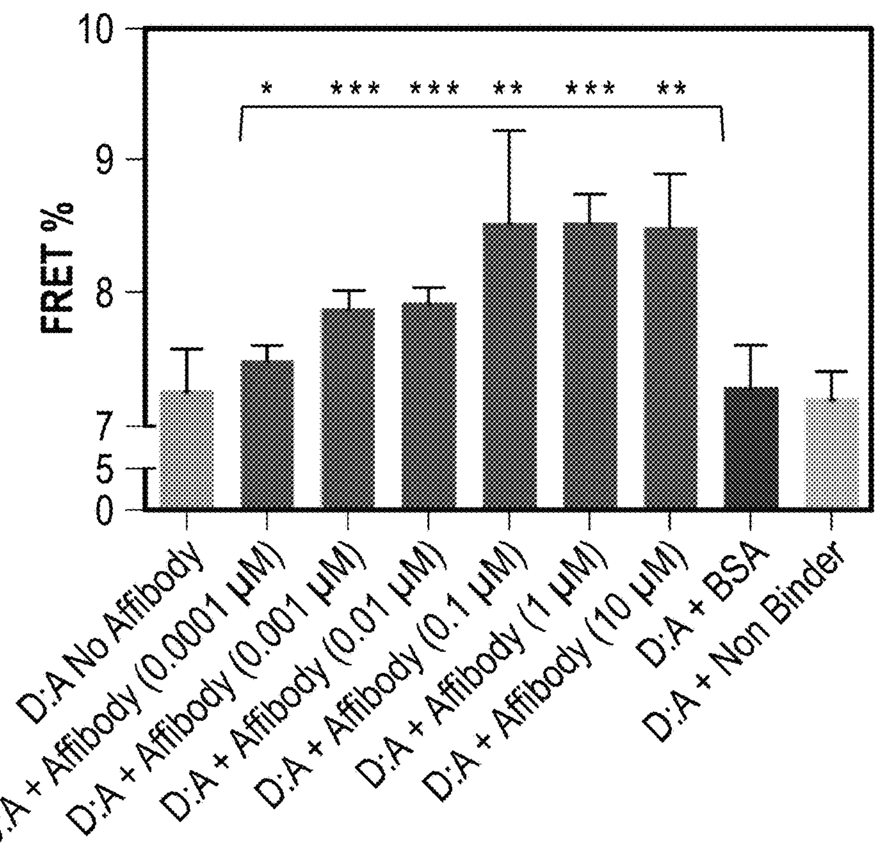
FIG. 5. Effect of $ABY_{DR5-6}$ on ligand-independent DR5-DR5 interactions. Effect of $ABY_{DR5-6}$ on ligand-independent DR5-DR5 interactions was determined using live-cell TR-FRET measurements. For lifetime measurements, HEK293 cells with a stable expression of DR5ΔCD-GFP and DR5ΔCD-GFP-RFP were lifted with trypsin, washed thrice with PBS, and resuspended in PBS at a concentration of 1 million cells/mL. Cells were treated with soluble $ABY_{DR5-6}$ (0.0001-10 μM), BSA and non-binder, and incubated for 1-2 hours. After incubation cells were washed with PBS and dispensed (50 μL/well) into a 96 well glass-bottom plate. Donor lifetime was measured using a fluorescence lifetime plate reader. Data are presented as mean±standard deviation of three independent experiments. Results were analyzed in Excel using a two-tailed unpaired t test. * indicates statistically significant with $p<0.05$,  indicates statistically significant with $p<0.01$, * indicates statistically significant with $p<0.001$.

Next, we evaluated the effect of soluble $ABY_{DR5-6}$ on ligand-independent DR5-DR5 interactions. It has been shown previously that several members of the TNF receptor superfamily, including DR5, TNFR1, and FAS, exist as ligand-independent oligomers (Clancy, L., et al., Proc Natl Acad Sci USA, 2005. 102(50): p. 18099-104; Siegel, R. M., et al., Science, 2000. 288(5475): p. 2354-7; Chan, F. K., et al., Science, 2000. 288(5475): p. 2351-4; Naismith, J. H., et al., J Biol Chem, 1995. 270(22): p. 13303-7). In our previous work, we established that it is possible to inhibit TRAIL-induced apoptosis by disrupting the DR5-DR5 interaction (Lo, C. H., et al., SLAS Discov, 2017: p. 2472555217706478; Vunnam, N., et al., J Mol Biol, 2017. 429(19): p. 2943-2953). So, we hypothesized that the anti-apoptotic effect of $ABY_{DR5-6}$ might be due to disruption of pre-ligand assembly of DR5 receptors. We therefore investigated the effect of $ABY_{DR5-6}$ on DR5-DR5 interactions using live-cell time-resolved Forster resonance energy transfer (TR-FRET). We previously showed that TR-FRET could directly report on receptor oligomerization (increase in FRET) and disruption of receptor-receptor interactions (decrease in FRET) (Vunnam, N., et al., J Mol Biol, 2017. 429(19): p. 2943-2953; Vunnam, N., et al., Biophys J, 2017. 113(2): p. 381-392). Experiments were carried out in HEK293 cells stably expressing the long isoform of DR5 without a cytoplasmic domain (DR5ΔCD) fused to GFP and co-expressing DR5ΔCD fused to GFP and RFP just downstream of the transmembrane domain of the receptors. DR5ΔCD-GFP (donor) lifetime in the presence and absence of acceptor (DR5ΔCD-RFP) was measured and then used to calculate FRET efficiency using Equation 1. Measurements showed a substantial decrease in the fluorescence lifetime of the donor in the presence of the acceptor compared with the donor only, which confirms efficient energy transfer between the FRET pairs. These results confirm that DR5 exists as ligand-independent oligomers. We then evaluated the effect of $ABY_{DR5-6}$ on DR5-DR5 interactions. Interestingly, cells treated with soluble $ABY_{DR5-6}$ showed higher FRET compared with untreated cells (FIG. 5). Increase in FRET suggests that upon $ABY_{DR5-6}$ binding DR5 undergoes conformational rearrangements that lead to a decrease in distance between the cytoplasmic ends of pre-assembled DR5 receptors. Cells treated with soluble bovine serum albumin or non-binder (negative controls) caused no significant FRET change compared with untreated cells (FIG. 5). These results suggest that $ABY_{DR5-6}$ does not block the DR5-DR5 interaction but rather modulates the local conformation. This local conformational change reduces apoptosis by inhibiting the recruitment of FADD to DR5 as shown in FIG. 3C. In concert with the earlier results (FIGS. 3 and 4), this modulation results in a less active conformation.

Effect of $ABY_{DR5-6}$ on Hepatocyte Lipoapoptosis in Huh-7 Cells

It has been shown that both TRAIL- and palmitate-induced apoptosis contributes to hepatocyte apoptosis in fatty liver disease (Hirsova, P. and G. J. Gores, Cell Mol Gastroenterol Hepatol, 2015. 1(1): p. 17-27; Cazanave, S. C. and G. J. Gores, Clin Lipidol, 2010. 5(1): p. 71-85; Cazanave, S. C., et al., J Biol Chem, 2011. 286(45): p. 39336-48). Therefore, we examined the effect of $ABY_{DR5-6}$ on TRAIL- and palmitate-induced apoptosis in Huh-7 cells, which is a well established in vitro model for studying hepatocyte lipoapoptosis in NAFLD (Hirsova, P. and G. J. Gores, Cell Mol Gastroenterol Hepatol, 2015. 1(1): p. 17-27). Huh-7 cells were treated with TRAIL in the presence and absence of $ABY_{DR5-6}$, and cell death was assessed using the MTT assay, the caspase-8 assay, and plate-based image cytometric analysis of Hoechst 33342 and SYTOX Green staining. Similar to the experiments in Jurkat cells, $ABY_{DR5-6}$ inhibited TRAIL-induced apoptosis in Huh-7 cells in a dose-dependent manner (FIG. 6A). $ABY_{DR5-6}$ consistently inhibited cell death as assessed by the maintenance of MTT activity, even at subnanomolar concentrations, whereas the nonbinder control yielded no protection (FIG. 9A).

Figures 9A, 9B, 9C:
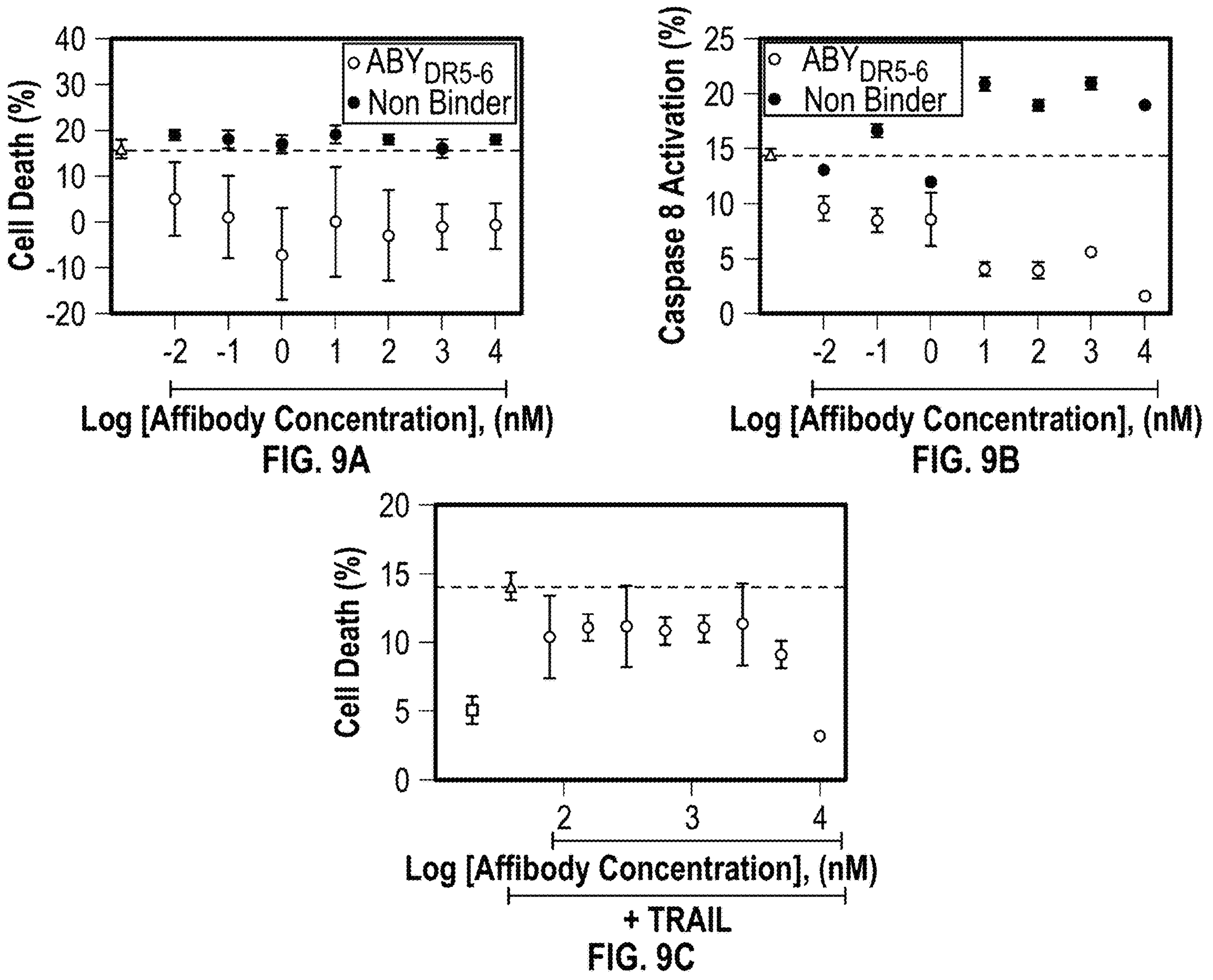
FIGS. 9A-9C. Effect of $ABY_{DR5-6}$ on TRAIL-induced apoptosis in Huh-7 hepatocytes. Huh-7 cells grown in 96-well plates were treated with recombinant human TRAIL (0.1 μg/mL) for 16 h in the presence or absence of increasing concentrations of $ABY_{DR5-6}$ (0.001 nM to 10 μM). TRAIL-induced cell death was determined by (FIG. 9A) the MTT assay, (FIG. 9B) the caspase-8 assay, and (FIG. 9C) a mixture of cell permeable Hoechst 33342 and impermeable Sytox Green DNA fluorescent dyes. Triangles and dotted lines represent TRAIL-induced cell death in the absence of affibody treatment, and squares represent cell death in untreated cells. Data are the mean±the standard deviation of three independent experiments. All $ABY_{DR5-6}$ samples have lower death (FIG. 9A) and caspase-8 activity (FIG. 9B) than nonbinder as determined by a two-tailed unpaired t test ($p<0.0001$).

$ABY_{DR5-6}$ inhibits caspase-8 activation in a dose-dependent manner with 50% inhibition at low nanomolar concentrations, whereas the nonbinder control has no effect (FIG. 9B). The Hoechst/SYTOX assay yields a more nuanced result (FIG. 9C). Moderate inhibition is observed at midnanomolar concentrations with more complete inhibition at low micromolar levels. Collectively, these results confirm that soluble $ABY_{DR5-6}$ protects Huh-7 cells from TRAIL-induced apoptosis.

Cellular stress, such as lipotoxicity or unmitigated endoplasmic reticulum stress, may induce apoptotic cell death via ligand-independent DR5 activation (Hirsova, P. and G. J. Gores, Cell Mol Gastroenterol Hepatol, 2015. 1(1): p. 17-27; Cazanave, S. C. and G. J. Gores, Clin Lipidol, 2010. 5(1): p. 71-85; Cazanave, S. C., et al., J Biol Chem, 2011. 286(45): p. 39336-48). To assess the effect of $ABY_{DR5-6}$ in ligand-independent induction of apoptosis, we employed a model of hepatocyte lipotoxicity in which fatty acid-induced cell death is largely mediated by DR5 (Hirsova, P. and G. J. Gores, Cell Mol Gastroenterol Hepatol, 2015. 1(1): p. 17-27). Huh-7 cells were treated with the fatty acid palmitate in the presence or absence of $ABY_{DR5-6}$. Huh-7 cells were stained with Hoechst 33342 and SYTOX Green staining and cell death was quantified using a plate-based image cytometer. Consistent with our other findings, $ABY_{DR5-6}$ inhibited palmitate-induced apoptosis in Huh-7 cells (FIG. 6B), suggesting that soluble $ABY_{DR5-6}$ can efficiently inhibit ligand-independent, DR5-mediated apoptosis. Taken together, our data clearly illustrate that $ABY_{DR5-6}$ is a noncompetitive DR5 antagonist.

Discussion

Currently, three therapeutic strategies are used to ameliorate TNF receptor related diseases: sequestration of ligand (Elliott, M. J., et al., Arthritis Rheum, 1993. 36(12): p. 1681-90; Mohler, K. M., et al., J Immunol, 1993. 151(3): p. 1548-61); competitive inhibition of ligand-receptor interactions (Ma, L., et al., J Biol Chem, 2014. 289(18): p. 12457-66; Davis, J. M. and J. Colangelo, Future Med Chem, 2013. 5(1): p. 69-79); and competitive inhibition of receptor-receptor interactions (Lo, C. H., et al., SLAS Discov, 2017: p. 2472555217706478; Vunnam, N., et al., J Mol Biol, 2017. 429(19): p. 2943-2953). While competitively targeting receptor assembly is a valid approach, we hypothesize superior efficacy via protein antagonists that stabilize an inactive receptor conformation without competing with ligand binding or receptor-receptor interactions. In this study we discovered a novel DR5 antagonist that acts in this non-competitive, allosteric manner.

Emerging evidence suggests that ligand-dependent and/or ligand-independent activation of DR5 signaling contributes to hepatocyte apoptosis, which is a key mechanism for disease progression in patients with fatty liver disease (Hirsova, P. and G. J. Gores, Cell Mol Gastroenterol Hepatol, 2015. 1(1): p. 17-27; Cazanave, S. C. and G. J. Gores, Clin Lipidol, 2010. 5(1): p. 71-85; Cazanave, S. C., et al., J Biol Chem, 2011. 286(45): p. 39336-48). Recently, several inhibitors of hepatic cell death have been suggested as potential treatment for NASH (Hajighasem, A., P. Farzanegi, and Z. Mazaheri, Arch Physiol Biochem, 2019. 125(2): p. 142-149). We propose that blocking DR5 apoptosis signaling pathway is a valuable approach in fatty liver disease therapy. Yeast display was used to select novel affibody molecules that selectively bind to human DR5. Since glycosylation of death receptors play an important role in receptor conformation and TRAIL-mediated apoptosis (Micheau, O., Int J Mol Sci, 2018. 19(3)), we expressed DR5 in mammalian cells during evolution of DR5 binders. Among enriched variants, one affibody molecule ($ABY_{DR5-6}$) strongly and selectively binds to the DR5 extracellular domain and showed biological activity in two different cell lines with three different cell-based assays. It is important to note that in all cell-based assays, $ABY_{DR5-6}$ produced similar efficacy, albeit at different potencies ($IC_{50}$). The variance in $IC_{50}$ could be attributed to the fundamental difference between the cell-based assays: the MTT assay monitors metabolic activity of cells; caspase-8 assay monitors extrinsic/receptor-mediated caspase-8 activity; and Hoechst/Sytox Green DNA fluorescent dyes measure the number of live and dead cells. Metabolic activity and cell viability represent two different aspects of cellular function, and both are required for the estimation of the physiological state of a cell after exposure to various types of stress. Nevertheless, these three distinct assays suggest that $ABY_{DR5-6}$ is an inhibitor of DR5 signaling.

Our biophysical and biochemical data show that the soluble $ABY_{DR5-6}$ binds to DR5 without blocking the ligand-receptor or the receptor-receptor interactions and triggers conformational changes in DR5 transmembrane (TM) domain-dimer. Previously we showed that TM-dimer of DR5 exists in open-active and closed-inactive conformations (Lewis, A. K., et al., Biophys J, 2014. 106(6): p. L21-4). Using TR-FRET, we previously demonstrated a conformational change in the DR5 TM-dimers upon ligand binding (Vunnam, N., et al., Biophys J, 2017. 113(2): p. 381-392) or soluble protein binding (Vunnam, N., et al., J Mol Biol, 2017. 429(19): p. 2943-2953). This phenomenon was also observed in other families of receptors (Jensen, A. D., et al., J Biol Chem, 2001. 276(12): p. 9279-90). Here, an increase in FRET efficiency upon $ABY_{DR5-6}$ binding suggests that the DR5 TM-dimer moved closer to each other. These findings confirm that the affibody is capable of binding the dimeric form of DR5, and binding of $ABY_{DR5-6}$ induces conformational changes in DR5 and favors the closed-inactive state of TM domain, which is in remarkable agreement with the functional assays.

Taken together, we discovered a novel, high-affinity and noncompetitive DR5 binder that attenuates TRAIL and palmitate-induced apoptosis in human Huh-7 cells. We believe that the $ABY_{DR5-6}$ molecule is a potential drug candidate for the treatment of fatty acid liver disease. $ABY_{DR5-6}$ provides valuable progression towards development of this novel noncompetitive, allosteric mode of TNF receptor antagonism.

Methods

Identification and Evolution of DR5 Specific ABY Binders Using Yeast Surface Display The naïve affibody library containing $2\times10^9$ variants was previously generated by designed diversification of 17 solvent-exposed amino acids located in helices 1 and 2 of the Z domain of protein A followed by introduction into a yeast display system (Woldring, D. R., et al., Biochemistry, 2017. 56(11): p. 1656-1671). The affibody yeast library was grown in SD-CAA (16.8 g/L sodium citrate dihydrate, 3.9 g/L citric acid, 20.0 g/L dextrose, 6.7 g/L yeast nitrogen base, 5.0 g/L casamino acids) at 30° C. with shaking. After 20 hours, yeast were centrifuged and resuspended in SG-CAA (10.2 g/L sodium phosphate dibasic heptahydrate, 8.6 g/L sodium phosphate monobasic monohydrate, 19.0 g/L galactose, 1.0 g/L dextrose, 6.7 g/L yeast nitrogen base, 5.0 g/L casamino acids) and grown overnight to induce affibody display on the yeast surface.

To discover affibody molecules that specifically bind to DR5, we performed magnetic activated cell sorting (MACS) and fluorescence-activated cell sorting (FACS). To target conformationally accurate DR5, sorts used cell lysates from HEK293 with a stable expression of long isoform of DR5 in which the cytoplasmic domain is replaced by GFP (DR5ΔCD-GFP). Magnetic sorts on the naïve library were performed at 4° C. with two washes during positive selections. For magnetic sorting, target and control proteins were conjugated to GFP-trap magnetic beads (40 μm magnetic beads coated in anti-GFP antibody. To coat the beads with proteins, HEK293 cells with stable expression of DR5ΔCD-GFP or transient expression of non-target protein (lymphocyte activation gene 3 (LAG3)-GFP) were detached, washed 3× with phosphate-buffered saline (PBS), and then lysed (2 mM EDTA, 1% Triton X-100, 1× protease inhibitor in PBS) on ice for 30 minutes. Cell lysates were centrifuged at 13000 rpm for 15 minutes at 4° C. to remove insoluble debris. Soluble supernatants were mixed with GFP-trap magnetic beads and incubated for 1-2 hours at 4° C. Beads were washed three times with PBS. Yeast displaying the ABY library were exposed to bare beads and beads with immobilized LAG3-GFP to remove any non-specific binding interactions. The remaining yeast were incubated with DR5ΔCD-GFP coated beads, and bound yeast were selected. These DR5-bound yeast populations were grown, induced, and sorted more stringently with another round of MACS with depletion on control beads and enrichment on DR5ΔCD-GFP coated beads with three washes. For FACS, DR5-bound yeast populations were induced, labeled with anti-c-Myc antibody, followed by AF647-conjugated anti-mouse antibody and DR5ΔCD-GFP lysate. All $GFP^+$/$AF647^+$ yeast cells were collected via BD FACS Aria II. Sorted yeast were grown, and plasmid DNA was extracted using Zymoprep Yeast Plasmid Miniprep Kit II.

Generation of Randomly Mutagenized ABY Library

Sorted DR5 binders were further engineered to increase binding affinity using random mutagenesis to the full gene and the helices of ABY in parallel by error-prone PCR using nucleotide analogues 2'-deoxy-P-nucleoside-5'-triphosphate and 8-oxo-2'-deoxyguanosine-5'-triphosphate (Woldring, D. R., et al., Biochemistry, 2017. 56(11): p. 1656-1671). The mutagenized gene fragments were transformed into yeast with homologous recombination with linearized pCT vector. The resultant mutant ABY population underwent two rounds of MACS and a FACS against mammalian cell lysates expressing DR5ΔCD-GFP (or LAG3-GFP for comparative control). Finally, FACS sorted ABY populations were labeled with mouse c-Myc antibody, followed by AF647-conjugated anti-mouse antibody and incubated with DR5ΔCD-GFP lysate (or LAG3 GFP lysate) for two hours at room temperature. Yeast clones, evaluated by flow cytometry, that showed double positive fluorescence signals (AF647+/GFP+) were collected, grown, and zymoprepped to isolate plasmid DNA. Plasmids were transformed into One Shot TOP10 *Escherichia coli* (Invitrogen) and sequenced by ACGT, Inc.

Cell Cultures and Reagents

HEK293 cells were cultured in phenol red-free Dulbecco's modified Eagle's medium with 2 mM L-glutamine; Jurkat cells were cultured in RPMI 1640 medium with 2 mM L-glutamine. Huh-7 were cultured in Dulbecco's modified Eagle's medium containing glucose (4.5 g/L). All media were supplemented with 10% fetal bovine serum, 100 U/mL penicillin, and 100 μg/mL streptomycin. Cells were cultured at 37° C., 5% C02. The N-terminal FLAG-tagged soluble TRAIL (residues 114-281) was overexpressed using the pT7-FLAG-1 expression system in *Escherichia coli* and purified by anti-FLAG-affinity column.

Molecular Biology cDNA encoding DR5ΔCD (1-240) was inserted at the N-terminus of the EGFP and TagRFP vectors (kind gift from David D. Thomas) using standard cloning techniques. To prevent dimerization, EGFP alanine 206 was mutated to lysine.

Overexpression and Purification of DR5 Binders

Evolved DR5-binding ABY variant sequences were transferred from pCT vector into pET expression vector with a C-terminal His6 tag (SEQ ID NO: 44) using NheI and BamHI restriction enzymes. Recombinant DR5 binders were overexpressed in *Escherichia coli*, purified by immobilized cobalt affinity chromatography, and analyzed by 4-20% SDS-PAGE under reducing conditions with Coomassie staining.

Binding Affinity Measurements of ABY Variants to DR5A CD-GFP on HEK293 Cells

HEK293 cells with stable expression of DR5ΔCD-GFP, TNFR1ΔCD-GFP or transient expression of LAG3-GFP or DR4ΔCD-GFP were detached using trypsin, washed with PBS, and incubated with soluble ABY variants at increasing concentrations for 2-4 hours at room temperature. Cells were washed with PBS with 0.1% bovine serum albumin to remove unbound affibody and labeled with AF647-conjugated anti-His5 antibody for 1-2 hours at 4° C. Fluorescence was analyzed on a BD Accuri C6 flow cytometer and quantified using FlowJo software.

Functional Assays

The effects of binders on biological functions of DR5 were assessed using three cell viability assays. For the 3-(4,5-dimethylthiazol-2-yl)-2,5-diphenyltetrazolium bromide (MTT) assay, Jurkat cells were seeded in 96-well plates at 5,000 cells/well. After being incubated at 37° C. for 24 hours, cells were treated with soluble affibodies for 2-4 hours and then treated with TRAIL (0.1 μg/mL) for 16 hours at 37° C. Cell viability was assessed with a Cytation 3 Cell Imaging Multi-Mode Reader luminometer.

For caspase-8 assays, Jurkat cells were seeded in 96-well plates at 5,000 cells/well. Cells were treated with soluble affibody, incubated for 1-2 h, and then treated with TRAIL (0.1 μg/mL), followed by 16 hours of incubation at 37° C. An equal volume of Caspase-Glo 8 reagent was added to each well, and the luminescence was measured after 30 min using a Cytation 3 Cell Imaging Multi-Mode Reader luminometer (BioTek).

For analysis of TRAIL-induced recruitment of FADD to DR5, Jurkat cells were treated with affibody (200 nM), incubated for 2-4 hours at 37° C., and then stimulated with FLAG-tagged TRAIL (0.1 μg/mL) for 4-6 hours. Post-stimulation cells were washed with cold PBS and lysed in RIPA buffer supplemented with protease inhibitors. Supernatants were transferred to a tube containing FLAG-tagged protein-bound anti-FLAG antibody-coated magnetic beads and rotated overnight at 4° C., followed by three washes with wash buffer (50 mM Tris-HCl [pH 7.5], 150 mM NaCl, 0.5% sodium deoxycholate, 1% NP-40). Immunoprecipitation samples were resolved using SDS-PAGE gels and subjected to Western blotting using anti-DR5 (Biolegend, 307302) and FADD (BD Biosciences, 610399) antibodies.

Cell Death Assay in Huh-7 Cells

Huh-7 cells grown in 96-well plates were treated with recombinant human TRAIL or palmitate (600 μM) for 16 h in 0-10 μm $ABY_{DR5-6}$. Palmitate was dissolved in isopropyl alcohol and conjugated to bovine serum albumin resuspended in DMEM media (10% bovine serum albumin) as previously described (Cazanave, S. C., et al., J Biol Chem, 2011. 286(45): p. 39336-48). Following incubation, cells were stained with cell permeable Hoechst 33342 and live cell-impermeant SYTOX Green to label all and dead cells, respectively. Stained cells were visualized, analyzed, and quantified using a plate-based image cytometer Celigo.

Pull-Down Assays

The effect of affibody on the TRAIL-DR5 interaction was determined by a pull-down assay with anti-GFP magnetic beads. DR5ΔCD-GFP lysate (from HEK293 cells with a stable expression of DR5ΔCD-GFP) was mixed with anti-GFP beads and incubated at 4° C. for 2 hours. The beads were washed thrice to remove the unbound proteins. Soluble TRAIL (1 μg/mL) or a mixture of TRAIL and affibody (200 μM) were added to DR5-GFP coated magnetic beads and rotated at 4° C. for 2-4 hours. Beads were washed thrice. Pulled down proteins were resolved by SDS-PAGE and then immunoblotted with anti-GFP, -TRAIL and -His5 antibodies.

Specificity of ABY variant to DR5 was determined by a pull-down assay with anti-His magnetic beads, soluble-DR4-Fc and soluble-DR5-Fc. Soluble $ABY_{DR5\text{-}6}$ (200 nM) was mixed with anti-His beads and incubated at 4° C. for 2 hours. The beads were then washed thrice to remove the unbound protein. Next, soluble-DR4-Fc (100 nM) or Soluble-DR5-Fc (100 nM) was added to $ABY_{DR5\text{-}6}$ coated magnetic beads and rotated at 4° C. for 2-4 hours. Then beads were washed thrice with PBS. Pulled-down proteins were resolved by SDS-PAGE and immunoblotted with anti-DR4 and anti-DR5 antibodies.

Fluorescence Lifetime Measurements

HEK293 cells with stable expression of DR5ΔCD-GFP and DR5ΔCD-GFP-RFP were grown in a 10 cm plate. For lifetime measurements, stable cells were detached with trypsin, washed thrice with PBS, treated with soluble DR5 binder (0-10 μM), and incubated for 1-2 hours. After incubation, cells were dispensed (50 μL/well) into a 96 well glass-bottom plate. Donor lifetime in the presence and absence of acceptor was measured by using a fluorescence lifetime plate reader. Time-resolved fluorescence waveforms for each well were fitted to single-exponential decays using least-squares minimization global analysis software to give donor lifetime (TD) and donor-acceptor lifetime (TDA). FRET efficiency (E) was then calculated based on Eq. (1)

$$E = 1 - \left(\frac{\tau_{DA}}{\tau_D}\right) \quad \text{(Equation 1)}$$

Colocalization of Affibody and DR5

To test the colocalization of soluble affibody with DR5, HEK293 cells with a stable expression of DR5ΔCD-GFP were grown on 35-mm glass bottom MatTek culture dishes and treated with soluble affibody and incubated for 2-4 h at 37° C. Cells were gently washed twice with PBS to remove the unbound soluble proteins and labeled with mouse His6-antibody, followed by AlexaFluor555-conjugated anti-mouse secondary antibody. Colocalization was evaluated using fluorescence microscopy.

Resource Table

| Reagent or Resource | Source | Identifier |
|---|---|---|
| Purified anti-human CD262 (DR5, TRAIL-R2) Antibody | Biolegend | Cat #307302 |
| Penta•His Alexa Fluor 647 Conjugate | Qiagen | Cat #35370 |
| Purified anti-His Tag Antibody | Biolegend | Cat #652520 |
| Recombinant Human TRAIL/TNFSF10 Protein | R&D systems | Cat #375-TL-010 |
| Soluble-DR4-Fc | Abcam | Cat #ab220558 |
| Soluble-DR5-Fc | Abcam | Cat #ab83547 |
| Anti-TRAIL antibody | Abcam | Cat #ab9959 |
| Purified Mouse Anti-Human FADD | BD Biosciences | Cat #610399 |
| Anti-GFP antibody | Abcam | Cat #ab290 |
| Rabbit Anti-Human DR5-UNLB | Southernbiotech | Cat #6600-01 |
| CD261 (DR4) Mouse anti-Human, Clone: DJR1, | eBioscience | Cat #14664482 |
| Goat anti-Mouse IgG (H + L) Highly Cross-Adsorbed Secondary Antibody | Thermo Fisher | Cat #A32727 |
| Palmitic acid | Sigma | Cat #5585 |
| Hoechst 33342 | Thermo Fisher | Cat #H1399 |
| SYTOX ™ Green Nucleic Acid Stain | Thermo Fisher | Cat #S7020 |
| Gibco ™ Penicillin Streptomycin (5,000 U/mL) | Thermo Fisher | Cat #15070063 |
| Gibco ™ L-Glutamine (200 mM) | Thermo Fisher | Cat #25030149 |
| RPMI-1640 Medium | ATCC | Cat #30-2001 |
| DMEM, high glucose, no glutamine, no phenol red | Thermo Fisher | Cat #31053028 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated anti-Death Receptor 5 (DR5) polypeptide, comprising one or more helix domains selected from the group consisting of:

(a) a helix 1 sequence comprising the amino acid sequence of any one of SEQ ID NOs: 1 to 6; and (b) a helix 2 sequence comprising the amino acid sequence of any one of SEQ ID NOs: 7 to 12.

2. The isolated polypeptide of claim 1, comprising:

(a) a helix 1 sequence comprising the amino acid sequence of any one of SEQ ID NOs: 1 to 6; and (b) a helix 2 sequence comprising the amino acid sequence of any one of SEQ ID NOs: 7 to 12.

3. The isolated polypeptide of claim 1, comprising:

a helix 1 sequence comprising the amino acid sequence of SEQ ID NO:6.

4. The isolated polypeptide of claim 1, comprising:

a helix 2 sequence comprising the amino acid sequence of SEQ ID NO:12.

5. An isolated anti-DR5 polypeptide, comprising:

(a) a helix 1 sequence comprising an amino acid sequence having at least 90% sequence identity to the amino acid sequence of SEQ ID NO:6; and (b) a helix 2 sequence comprising an amino acid sequence having at least 90% sequence identity to the amino acid sequence of SEQ ID NO: 12.

6. The isolated polypeptide of claim 1, comprising:

(a) a helix 1 sequence comprising the amino acid sequence of SEQ ID NO:6; and (b) a helix 2 sequence comprising the amino acid sequence of SEQ ID NO: 12.

7. The isolated polypeptide of claim 1, comprising an amino acid sequence that has at least 85% sequence identity to any one of SEQ ID NOs: 29-34 and 41.

8. The isolated polypeptide of claim 7, comprising the amino acid sequence of any one of SEQ ID NOs: 29-34 and 41.

9. The isolated polypeptide of claim 6, comprising an amino acid sequence that has at least 85% sequence identity to the amino acid sequence of SEQ ID NO: 34.

10. The isolated polypeptide of claim 7, comprising the amino acid sequence of SEQ ID NO:34.

11. The isolated polypeptide of claim 1, further comprising a helix 3 sequence comprising the amino acid sequence of any one of SEQ ID NOs: 13-14.

12. A composition comprising the isolated polypeptide of claim 1, and a carrier.

13. An isolated nucleic acid comprising a nucleotide sequence encoding the isolated polypeptide of claim 1.

14. A vector comprising the nucleic acid of claim 13.

15. A cell comprising the nucleic acid of claim 13.

16. A method of inhibiting the activity of DR5, comprising contacting DR5 with the isolated polypeptide of claim 1.

17. A method for treating a fatty liver disorder in a mammal, comprising administering an effective amount of the isolated polypeptide of claim 1 to the mammal.

18. A Kit comprising the isolated polypeptide of claim 1, packaging material, and instructions for administering the isolated polypeptide to a mammal to treat a fatty liver disease disorder.

19. The isolated polypeptide of claim 5, comprising an amino acid sequence that has at least 90% sequence identity to the amino acid sequence of SEQ ID NO:34.

20. The isolated polypeptide of claim 19, comprising an amino acid sequence that has at least 95% sequence identity to the amino acid sequence of SEQ ID NO:34.

* * * * *

SEQUENCE LISTING

```
<160> NUMBER OF SEQ ID NOS: 44

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Gln Gly Tyr Ala Gly Arg Glu Ile Arg Leu
```

1 5 10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Glu Lys Leu Asp Ala Tyr Pro Val Ile Glu Asp
1 5 10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Glu Arg Glu Phe Ala Val Leu Glu Ile Ser Leu
1 5 10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Glu Gly Glu Val Ala Gly Ala Glu Ile Thr Val
1 5 10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Glu Ser Thr Leu Ala Glu Ile Glu Ile Leu Arg
1 5 10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Glu Asp Tyr Leu Ala Val Val Glu Ile Val Gly
1 5 10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Pro Gln Gly Gly Ala Phe Ile Gly Ala Leu Ala Asp
1 5 10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Glu Gln Val Met Ala Phe Ile Val Ala Leu Glu Asn
1 5 10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Val Gln Ser Leu Ala Phe Ile Pro Ala Leu Gly Asp
1 5 10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Gly Gln Ala Gly Ala Phe Ile Gln Ala Leu Leu Asp
1 5 10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ala Gln Ile Tyr Ala Phe Ile Leu Ala Leu Thr Asp
1 5 10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Gly Gln Thr Leu Ala Phe Ile Phe Ala Leu Gly Asp
1 5 10

<210> SEQ ID NO 13

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Glu Leu Leu Ser Glu Ala Lys Lys Leu Asn Asp Ser
1               5                   10


<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Asn Leu Leu Ala Glu Ala Lys Lys Leu Asn Asp Ala
1               5                   10


<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Glu Ala Lys Tyr Ala Lys
1               5


<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Asp Asn Lys Phe Asn Lys
1               5


<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Pro Asn Leu Thr Asn
1               5


<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Leu Pro Asn Leu Thr Arg
1               5


<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Asn Leu Thr Leu
1               5


<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Pro Asn Leu Thr Asp
1               5


<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Pro Asn Leu Thr Cys
1               5


<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Pro Asn Leu Asn Glu
1               5


<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Pro Asn Leu Asn Trp
1               5


<210> SEQ ID NO 24
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 24

Leu Pro Asn Leu Asn Val
1               5


<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Pro Asn Leu Asn Asn
1               5


<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Pro Asn Leu Asn Asn
1               5


<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Pro Ser Gln Ser
1               5


<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ala Pro Lys
1


<210> SEQ ID NO 29
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Glu Ala Lys Tyr Ala Lys Glu Gln Gly Tyr Ala Gly Arg Glu Ile
1               5                   10                  15

Arg Leu Leu Pro Asn Leu Thr Arg Pro Gln Gly Gly Ala Phe Ile Gly
```

```
            20                  25                  30

Ala Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 30
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Glu Ala Lys Tyr Ala Lys Glu Lys Leu Asp Ala Tyr Pro Val Ile
1               5                   10                  15

Glu Asp Leu Pro Asn Leu Thr Leu Glu Gln Val Met Ala Phe Ile Val
            20                  25                  30

Ala Leu Glu Asn Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 31
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Glu Ala Lys Tyr Ala Lys Glu Arg Glu Phe Ala Val Leu Glu Ile
1               5                   10                  15

Ser Leu Leu Pro Asn Leu Thr Asp Val Gln Ser Leu Ala Phe Ile Pro
            20                  25                  30

Ala Leu Gly Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 32
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Glu Ala Lys Tyr Ala Lys Glu Gly Glu Val Ala Gly Ala Glu Ile
1               5                   10                  15

Thr Val Leu Pro Asn Leu Thr Cys Gly Gln Ala Gly Ala Phe Ile Gln
            20                  25                  30

Ala Leu Leu Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 33
```

<211> LENGTH: 58
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Ala Glu Ala Lys Tyr Ala Lys Glu Ser Thr Leu Ala Glu Ile Glu Ile
1               5                   10                  15

Leu Arg Leu Pro Asn Leu Thr Asn Ala Gln Ile Tyr Ala Phe Ile Leu
            20                  25                  30

Ala Leu Thr Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 34
<211> LENGTH: 58
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Ala Glu Ala Lys Tyr Ala Lys Glu Asp Tyr Leu Ala Val Val Glu Ile
1               5                   10                  15

Val Gly Leu Pro Asn Leu Thr Leu Gly Gln Thr Leu Ala Phe Ile Phe
            20                  25                  30

Ala Leu Gly Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 35
<211> LENGTH: 174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
gccgaagcaa aatacgctaa agaacagggg tatgcggggc gtgaaatcag gctgctgccg     60

aacctgaccc ggcctcaggg gggtgcattc ataggggcac tggctgatga cccgtcccag    120

agctctgaac tcctgtctga ggcgaagaaa ctgaacgatt cccaagcacc aaaa          174
```

<210> SEQ ID NO 36
<211> LENGTH: 174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gccgaagcaa aatacaacaa agaaaagttg gacgcgtacc ccgtgatcga ggacctgccg     60

aacctgaccc tcgagcaggt gatggcattc atcgtggcac tggagaacga cccgtcccag    120

agctctgaac tcctgtctga ggcgaagaaa ctgaacgatt cccaagcacc aaaa          174
```

<210> SEQ ID NO 37
<211> LENGTH: 174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
gccgaagcga aatacgctaa agaacgggag tttgcggttt tggaaatcag tttgctgccg 60
aacctgaccg atgtgcagag tttggcattc atacctgcac tgggtgatga cccgtcccag 120
agctctgaac tcctgtctga ggcgaagaaa ctgaacgatt cccaagcacc aaaa 174

<210> SEQ ID NO 38
<211> LENGTH: 174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38
gccgaagcga aatacgctaa agaaggggag gtggcggggg cggaaatcac ggttctgccg 60
aacctgacct gtgggcaggc gggggcattc atacaggcac tgctggatga cccgtcccag 120
agctctgaac tcctgtctga ggcgaagaaa ctgaacgatt cccaagcacc aaag 174

<210> SEQ ID NO 39
<211> LENGTH: 174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39
gccgaagcaa aatacgctaa agaatctacg ttggcggaga ttgaaatcct gcgtctgccg 60
aacctgacca atgcgcagat ttatgcattc atacttgcac tgactgatga cccgtcccag 120
agctctgaac tcctgtctga ggcgaagaaa ctgaacgatt cccaagcacc aaaa 174

<210> SEQ ID NO 40
<211> LENGTH: 174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
gccgaagcaa aatacgctaa agaagattat ttggcggtgg tggaaatcgt ggggctgccg 60
aacctgaccc ttggtcagac tctggcattc atatttgcac tgggtgatga cccgtcccag 120
agctctgaac tcctgtctga ggcgaagaaa ctgaacgatt cccaagcacc aaaa 174

<210> SEQ ID NO 41
<211> LENGTH: 58
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Ala Glu Ala Lys Tyr Asn Lys Glu Lys Leu Asp Ala Tyr Pro Val Ile

```
1               5                   10                  15

Glu Asp Leu Pro Asn Leu Thr Leu Glu Gln Val Met Ala Phe Ile Val
            20                  25                  30

Ala Leu Glu Asn Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Glu Ala Lys Tyr Asn Lys
1               5


<210> SEQ ID NO 43
<211> LENGTH: 58
<212> TYPE: PRT
<213> ORGANISM: Unknown
<220> FEATURE:
<223> OTHER INFORMATION: Description of Unknown:
      wild-type affibody

<400> SEQUENCE: 43

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 44

His His His His His His
1               5
```